(12) United States Patent
Kawakami

(10) Patent No.: US 11,576,564 B2
(45) Date of Patent: Feb. 14, 2023

(54) OBJECTIVE OPTICAL SYSTEM FOR ENDOSCOPE

(71) Applicant: OLYMPUS CORPORATION, Hachioji (JP)

(72) Inventor: Yoshihiro Kawakami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 945 days.

(21) Appl. No.: 16/413,081

(22) Filed: May 15, 2019

(65) Prior Publication Data

US 2019/0261834 A1 Aug. 29, 2019

Related U.S. Application Data

(63) Continuation of application No. PCT/JP2017/044124, filed on Dec. 8, 2017.

(30) Foreign Application Priority Data

Dec. 21, 2016 (JP) .............................. JP2016-247682

(51) Int. Cl.
*A61B 1/04* (2006.01)
*A61B 1/00* (2006.01)
(Continued)

(52) U.S. Cl.
CPC .......... *A61B 1/046* (2022.02); *A61B 1/00096* (2013.01); *A61B 1/00174* (2013.01);
(Continued)

(58) Field of Classification Search
CPC ............ A61B 1/00096; A61B 1/00174; A61B 1/0623; A61B 1/04; A61B 1/046; A61B 1/0011; G02B 13/04; G02B 23/243
See application file for complete search history.

(56) References Cited

U.S. PATENT DOCUMENTS 5,916,148 A 6/1999 Tsuyuki
6,206,825 B1 3/2001 Tsuyuki
(Continued)

FOREIGN PATENT DOCUMENTS

JP 09010170 A 1/1997
JP 2006178242 A 7/2006
(Continued)

OTHER PUBLICATIONS

International Preliminary Report on Patentability (IPRP) (and English language translation thereof) and Written Opinion dated Jul. 4, 2019 issued in counterpart International Application No. PCT/JP2017/044124.

(Continued)

*Primary Examiner* — Nasim N Nirjhar
(74) *Attorney, Agent, or Firm* — Holtz, Holtz & Volek PC

(57) ABSTRACT

An objective optical system for endoscope consists of a front group having a negative refractive power, an aperture stop, and a rear group having a positive refractive power. The front group consists of a first lens having a negative refractive power and a second lens having a positive refractive power. The rear group consists of a third lens having a positive refractive power, a cemented lens of a fourth lens having a positive refractive power and a fifth lens having a negative refractive power, and a sixth lens having a positive refractive power. A shape of the second lens is a meniscus shape having a convex surface directed toward an image side. The sixth lens is cemented to a plane parallel plate, and the following conditional expressions (1) and (2) are satisfied:

$1.0 < f3/d6 < 2.8$ (1)

$1.7 < |f1/f| < 10$ (2).

9 Claims, 13 Drawing Sheets

(51) Int. Cl.
    *A61B 1/06*     (2006.01)
    *G02B 13/04*     (2006.01)
    *G02B 23/24*     (2006.01)

(52) U.S. Cl.
    CPC ............ *A61B 1/0623* (2013.01); *G02B 13/04* (2013.01); *G02B 23/243* (2013.01)

(56) References Cited

U.S. PATENT DOCUMENTS

| | | |
|---|---|---|
| 2008/0158688 A1 | 7/2008 | Ohtake et al. |
| 2012/0127598 A1 | 5/2012 | Katahira |
| 2012/0154932 A1 | 6/2012 | Katahira |
| 2016/0306162 A1 | 10/2016 | Ushio |
| 2017/0153416 A1* | 6/2017 | Hsieh ................. G02B 13/0045 |
| 2019/0053695 A1* | 2/2019 | Fujii ..................... G02B 15/24 |

FOREIGN PATENT DOCUMENTS

| | | |
|---|---|---|
| JP | 2008164724 A | 7/2008 |
| JP | 5927368 B1 | 6/2016 |
| WO | 2011077972 A1 | 6/2011 |
| WO | 2011125539 A1 | 10/2011 |
| WO | 2016031586 A1 | 3/2016 |

OTHER PUBLICATIONS

International Search Report (ISR) dated Mar. 13, 2018 issued in International Application No. PCT/JP2017/044124.
Written Opinion dated Mar. 13, 2018 issued in International Application No. PCT/JP2017/044124.

* cited by examiner

OBJECTIVE OPTICAL SYSTEM FOR ENDOSCOPE

CROSS-REFERENCE TO RELATED APPLICATION

The present application is a continuation application of PCT/JP2017/044124 filed on Dec. 8, 2017 which is based upon and claims the benefit of priority from Japanese Patent Application No. 2016-247682 filed on Dec. 21, 2016; the entire contents of which are incorporated herein by reference.

BACKGROUND OF THE INVENTION

Field of the Invention

The present invention relates to an objective optical system, and particularly, to an objective optical system for endoscope which is used a medical endoscope.

Description of the Related Art

In recent years, for reducing stress on a patient and improving a diagnosis performance, an endoscope having a small size with a wide angle of view and a high image quality has been sought as a medical endoscope. Therefore, in an image pickup element to be installed in an endoscope, a pixel pitch and a size of the image pickup element have been becoming smaller year by year. With this, it is necessary to satisfy optical performance such as widening of the angle of view and aberration correction, while making an objective optical system for endoscope small-sized.

When the pixel pitch is made small and an image height is made small with the number of pixels maintained to be same as before, it is possible to make an optical system also relatively small-sized. However, when an aperture stop is also made small-sized similarly, an image resolution is degraded due to an effect of diffraction. Therefore, a bright optical system with a small F-number is necessary. In general, in a bright optical system, besides that an aberration correction is difficult, a depth of field becomes narrow. In such optical system, the optical performance is degraded due to a focal shift because of a manufacturing variation in a cure-shrinkage of an adhesive.

Furthermore, regarding the lens or the image pickup element, when a shift in a direction perpendicular to an optical axis occurs, with the image height becoming smaller, a shift in asymmetry of an angle of view (hereinafter, referred to as 'angle of deviation') with respect to the same amount of shift becomes large. Therefore, in a process of assembling the objective optical system for endoscope, a highly accurate adjustment at the time of adjusting a center position of the image pickup element of the optical system becomes necessary. Consequently, this leads to an increase in the cost and a degradation of productivity due to a degradation of workability. Moreover, even when the position adjustment could be done with high accuracy, when there is a shift in the position of the image pickup element due to the cure-shrinkage of adhesive, a balance of the angle of view after curing of adhesive is disrupted.

Particularly, in an objective optical system for endoscope with a wide angle of view of about 160°, an angle of incidence of light incident on a front-end lens is large. Consequently, there has been a problem of degradation of an optical performance due to occurrence of vignetting at a peripheral portion of an image by peripheral darkening associated with an increase in a reflectance at a surface of incidence.

Moreover, when a shift in an optical axial direction occurs in a lens position in a similar manner, there is also a shift occurring in the angle of view. In an objective optical system for endoscope, generally, a barrel distortion is generated, and by increasing a magnification at a center of an image field, an image of a peripheral area of the image field is made to be distorted. When the shift in the optical axial direction occurs in a lens and an optical magnification has fluctuated, in a case of having the barrel distortion, the distortion of image in the peripheral area of the image field is large. Consequently, an amount of a variation in the angle of view also becomes large. When the angle of view is widened to about 160°, the distortion of the image in the peripheral area of the image field becomes even larger, and as a result the shift in the angle of view also becomes large. Even in this case, the vignetting is susceptible to occur in the peripheral portion of the image field in a similar manner.

As described heretofore, in an objective optical system for endoscope with a wide angle of view, it is necessary to suppress the shift in the angle of deviation and the shift in the angle of view due to a variation at the process of assembling the objective optical system, and to prevent the vignetting in the peripheral portion of the image field.

In Japanese Patent Publication No. 5927368, an objective optical system for endoscope has been proposed. In the objective optical system for endoscope, an effect of the focal shift is suppressed, while keeping small-sized and with a high image quality. Moreover, in the endoscope objective optical system, sensitivity with respect to the focal shift is lowered by disposing a positive lens immediately after on an image side of a space for focusing adjustment, and thereby it is possible to achieve a high-definition image quality.

Moreover, in Japanese Patent Application Laid-open Publication No. 2006-178242 and Japanese Patent Application Laid-open Publication No. 2008-164724, zoom lenses in which the correction of various aberrations is favorable while small-sizing by making an arrangement of lenses appropriately and setting the refractive power suitably, have been disclosed.

SUMMARY OF THE INVENTION

An objective optical system for endoscope according to at least some embodiments of the present invention consists of in order from an object side, a front group having a negative refractive power, an aperture stop, and a rear group having a positive refractive power, wherein the front group consists of a first lens which is a single lens having a negative refractive power and a second lens which is a single lens having a positive refractive power, the rear group consists of a third lens which is a single lens having a positive refractive power, a cemented lens of a fourth lens having a positive refractive power and a fifth lens having a negative refractive power, and a sixth lens having a positive refractive power, an object-side surface of the first lens is a flat surface, and a shape of the second lens is a meniscus shape having a convex surface directed toward an image side, the sixth lens is cemented to a plane parallel plate, and the following conditional expressions (1) and (2) are satisfied:

$$1.0 < f3/d6 < 2.8 \quad (1)$$

$$1.7 < |f1/f| < 10 \quad (2)$$

where, f3 denotes a focal length of the third lens;

d6 denotes a thickness of the sixth lens, f1 denotes a focal length of the first lens, and f denotes a focal length of the overall objective optical system for endoscope.

DETAILED DESCRIPTION OF THE INVENTION

An objective optical system for endoscope according to the present embodiments will be described below in detail by referring to the accompanying diagrams. However, the present invention is not restricted to the embodiments and the examples described below.

Figure 1:
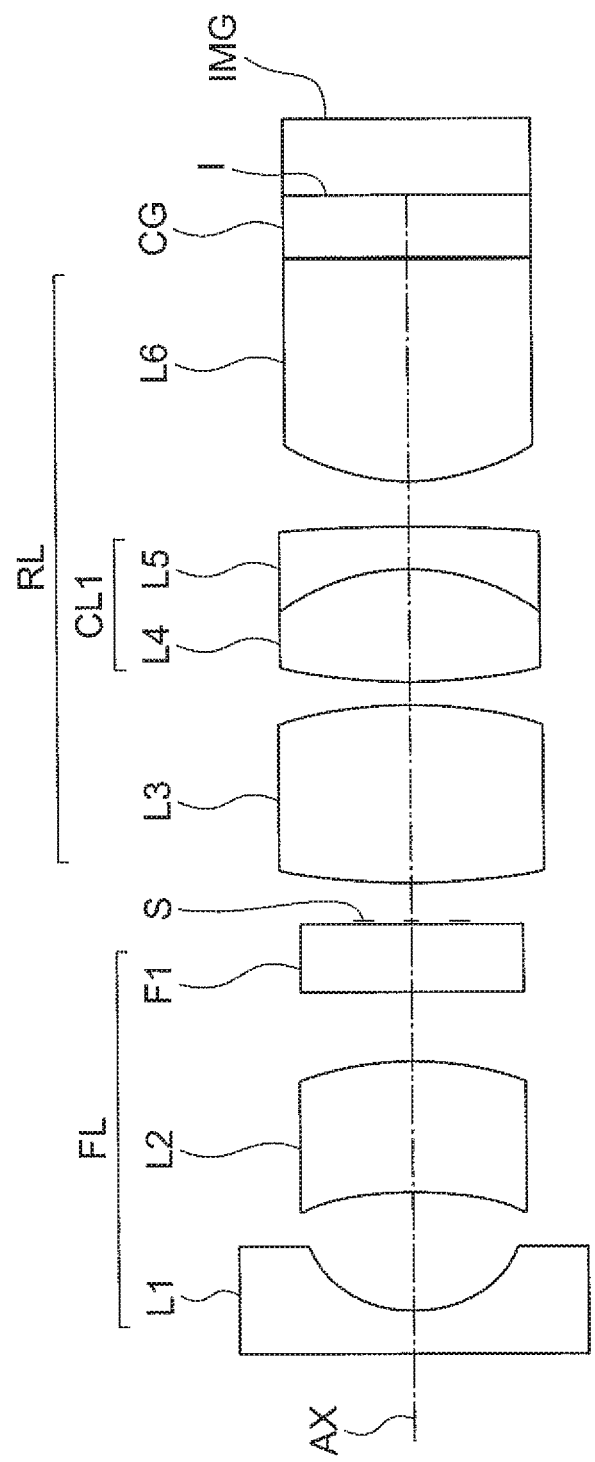
FIG. 1 is a diagram showing a cross-sectional view of a lens arrangement of an objective optical system for endoscope according to an embodiment of the present invention.

FIG. 1 is a diagram showing a cross-sectional view of a lens arrangement of an objective optical system for endoscope according to an embodiment of the present invention.

The objective optical system for endoscope according to the present embodiment includes in order from an object side, a front group FL having a negative refractive power, an aperture stop S, and a rear group RL having a positive refractive power, wherein the front group includes a first lens L1 which is a single lens having a negative refractive power and a second lens L2 which is a single lens having a positive refractive power, and the rear group RL includes a third lens L3 which is a single lens having a positive refractive power, a cemented lens CL1 of a fourth lens L4 having a positive refractive power and a fifth lens L5 having a negative refractive power, and a sixth lens L6 having a positive refractive power, and an object-side surface of the first lens L1 is a flat surface, and a shape of the second lens L2 is a meniscus shape having a convex surface directed toward an image side, and the sixth lens L6 is cemented to a plane parallel plate, and the following conditional expressions (1) and (2) are satisfied:

$$1.0 < f3/d6 < 2.8 \quad (1)$$

$$1.7 < |f1/f| < 10 \quad (2)$$

where, f3 denotes a focal length of the third lens L3;

d6 denotes a thickness of the sixth lens L6, f1 denotes a focal length of the first lens L1, and f denotes a focal length of the overall objective optical system for endoscope.

Moreover, a plane parallel plate such as a cover glass CG for preventing the image pickup element IMG from getting any scratches etc. is affixed to an image pickup surface I of the image pickup element IMG. The sixth lens L6 is cemented to the cover glass CG. Consequently, the sixth lens L6 is cemented to the image pickup element IMG.

By disposing the front group FL having a negative refractive power, the aperture stop S, and the rear group RL having a positive refractive power in order from the object side, since an optical system becomes an optical system of a retro focus type, according to an arrangement of the present embodiment, widening of an angle of view becomes possible.

Moreover, as a lens in the front group FL, by disposing the first lens L1 having a negative refractive power of which the object side is a flat surface, it is possible to reduce a risk of cracking of lens due to a shock and a water removal at the time of observation. Furthermore, by disposing the second lens L2 having a positive refractive power and a meniscus-shape with a convex surface directed toward the image side, it is possible to make a lens diameter small while correcting an aberration which occurs in the first lens L1. As a result, it is possible to provide an objective optical system for endoscope which is small-sized and which is suitable for an endoscope.

Moreover, as a lens in the rear group RL, the third lens L3 having a comparatively larger positive refractive power is disposed for forming a positive refractive power of the retro focus. Furthermore, the cemented lens CL1 of the fourth lens L4 having a positive refractive power and the fifth lens L5 having negative refractive power is disposed at a position at which a light ray height becomes high. By such arrangement, it is possible to correct a chromatic aberration favorably.

By disposing the sixth lens L6 having a positive refractive power upon cementing to the image pickup element IMG, an optical magnification from the first lens L1 up to the fifth lens L5 is made relatively small. Accordingly, it is possible to alleviate sensitivity of a focal shift and to suppress a degradation of an optical performance due to the focal shift.

Furthermore, for achieving widening of angle of view, small-sizing and high-quality image while suppressing the degradation of the optical performance by reducing a shift in the angle of deviation and a shift in focus due to a manufacturing variation at the process of assembling the objective optical system, it is desirable to make an arrangement such that conditional expressions (1) and (2) are satisfied, in addition to making the abovementioned arrangement.

To start with, for reducing the shift in the angle of deviation and the shift in focus due to the manufacturing variation, it is necessary to set an arrangement of the sixth lens L6. When the refractive power of the sixth lens L6 is made large, either a longitudinal magnification or a lateral magnification becomes small with respect to a variation in a distance between the fifth lens L5 and the sixth lens L6. Consequently, reduction of the shift in focus and reduction of the shift in angle of deviation become possible.

However, when a focal length of the sixth lens L6 is made small for cementing to the image pickup element IMG, a radius of curvature on the object side becomes small. Consequently, performance in a peripheral portion of image field, and particularly, a curvature of field and an astigmatism are degraded.

Therefore, in the present embodiment, the shift in focus and the shift in the angle of deviation are reduced by keeping away a curved surface of the sixth lens L6 from the image pickup surface I and making the longitudinal magnification large. However, when the curved surface of the sixth lens L6 is kept away from the image pickup surface I, a thickness of the sixth lens L6 becomes large, and therefore a total length of the optical system becomes large.

Therefore, in the present embodiment, regarding the shift in focus and the shift in the angle of deviation, and the total length of the optical system, it is desirable that the following conditional expression (1) be satisfied.

$$1.0 < f3/d6 < 2.8 \tag{1}$$

Conditional expression (1) is related to an appropriate ratio of f3 and d6. In a case of exceeding an upper limit value of conditional expression (1), the thickness of the sixth lens L6 becomes excessively thin. Consequently, the shift in focus and the shift in the angle of deviation become large, or the curvature of field and the astigmatism are deteriorated.

In a case of falling below a lower limit value of conditional expression (1), the thickness of the sixth lens L6 becomes excessively thick. Consequently, a requirement of small-sizing cannot be fulfilled.

Next, for reducing a shift in an angle of view due to the manufacturing variation, it is necessary to set an arrangement of the first lens L1. In a case in which the abovementioned lens arrangement is made, a distance from the first lens L1 up to the second lens L2 becomes largely effective in a fluctuation of the angle of view.

Therefore, in the present embodiment, the refractive power of the first lens L1 is set appropriately, in particular. Here, the first lens L1 has a negative refractive power necessary for making an optical system of a retro focus type. Therefore, the negative refractive power of the first lens L1 has a substantial effect on the total length of the optical system and a lens diameter.

Therefore, in the present embodiment, regarding the shift in the angle of view and the total length of the optical system, it is desirable that the following conditional expression (2) be satisfied.

$$1.7 < |f1/f| < 10 \tag{2}$$

Conditional expression (2) is related to an appropriate ratio of f1 and f. In a case of exceeding an upper limit value of conditional expression (2), the refractive power of the first lens L1 becomes excessively small. In this case, since the total length of the optical system and the lens diameter become large, it is not possible to make the optical system small-sized.

In a case of falling below a lower limit value of conditional expression (2), the refractive power of the first lens L1 becomes excessively large. Consequently, the fluctuation in the angle of view due to the manufacturing variation becomes large.

It is preferable that the following conditional expression (1') be satisfied instead of conditional expression (1).

$$1.2 < f3/d6 < 2.7 \tag{1'}$$

It is more preferable that the following conditional expression (1") be satisfied instead of conditional expression (1) or (1').

$$1.6 < f3/d6 < 2.6 \tag{1"}$$

It is preferable that the following conditional expression (2') be satisfied instead of conditional expression (2).

$$1.7 < |f1/f| < 5.0 \tag{2'}$$

It is more preferable that the following conditional expression (2") be satisfied instead of conditional expression (2) or (2').

$$1.7 < |f1/f| < 1.9 \tag{2"}$$

Moreover, according to a preferable aspect of the present embodiment, it is preferable that the following conditional expression (3) be satisfied:

$$-5.0 < f35/f12 < -1.3 \tag{3}$$

where, f35 denotes a combined focal length of lenses from the third lens L3 up to the fifth lens L5, and f12 denotes a combined focal length of lenses from the first lens L1 up to the second lens L2.

Conditional expression (3) is related to an appropriate ratio of f35 and f12. By satisfying conditional expression (3), it is possible to regulate appropriately the arrangement of the refractive power of the front group FL and the rear group RL. Consequently, it is possible to correct the curvature of field favorably, and to achieve a high image quality.

In a case of exceeding an upper limit value of conditional expression (3), f12 becomes relatively large. In this case, since the refractive power of the front group FL becomes small, it becomes difficult to make the total length of the optical system small.

In a case of falling below a lower limit value of conditional expression (3), f12 becomes relatively small. In this case, since the refractive power of the front group FL becomes large, the shift in the angle of view is susceptible to occur.

It is more preferable that the following conditional expression (3') be satisfied instead of conditional expression (3).

$$-4.0<f35/f12<-1.4 \quad (3')$$

It is even more preferable that the following conditional expression (3") be satisfied instead of conditional expression (3) or (3').

$$-2.0<f35/f12<-1.5 \quad (3")$$

Moreover, according to a preferable aspect of the present embodiment, it is preferable that the following conditional expression (4) is satisfied:

$$0.5<R6L/R1R<2.4 \quad (4)$$

where,

R6L denotes a radius of curvature of an object side of the sixth lens L6, and

R1R denotes a radius of curvature of an image side of the first lens L1.

Conditional expression (4) is related to an appropriate ratio of R6L and R1R. Moreover, conditional expression (4) is related to the radius of curvature of the first lens L1 and the radius of curvature of the sixth lens L6. By satisfying conditional expression (4), since it is possible to regulate appropriately the arrangement of refractive power of the first lens L1 and the sixth lens L6, while securing a workability of lenses, it is possible to correct a coma aberration and the chromatic aberration favorably.

In a case of exceeding an upper limit value of conditional expression (4), since the refractive power of the sixth lens L6 becomes small, the shift in focus and the shift in the angle of deviation are susceptible to occur. Therefore, it is not preferable to exceed the upper limit value of conditional expression (4). Moreover, since the radius of curvature of the first lens L1 becomes small, correction of the coma aberration becomes difficult. Furthermore, since a shape of the lens surface becomes closer to a hemispherical shape, the workability of lens is degraded.

In a case of falling below a lower limit value of conditional expression (4), since the refractive power of the first lens L1 becomes small, it becomes difficult to make the diameter of the first lens L1 small. Therefore, it is not preferable to fall below the lower limit value of conditional expression (4). Moreover, the radius of curvature of the sixth lens L6 becomes small. In this case, since the chromatic aberration occurs, it becomes difficult to achieve a favorable image quality.

It is more preferable that the following conditional expression (4') be satisfied instead of conditional expression (4).

$$1.0<R6L/R1R<2.2 \quad (4')$$

It is even more preferable that the following conditional expression (4") be satisfied instead of conditional expression (4) or (4').

$$1.7<R6L/R1R<2.1 \quad (4")$$

Moreover, according to a preferable aspect of the present embodiment, it be preferable that the following conditional expression (5) is satisfied:

$$1.5<f15/f<5.0 \quad (5)$$

where, f15 denotes a combined focal length of lenses from the first lens L1 up to the fifth lens L5, and f denotes the focal length of the overall objective optical system for endoscope.

Conditional expression (5) is related to an appropriate ratio of f15 and f. Moreover, conditional expression (5) is a conditional expression related to the refractive power of lenses from the first lens L1 up to the fifth lens L5.

By satisfying conditional expression (5), it is possible to suppress a degradation of image quality due to the manufacturing variation and to achieve a high-definition image quality while achieving small-sizing by an appropriate arrangement of the refractive power of the lenses and a favorable correction of the curvature of field.

In a case of exceeding an upper limit value of conditional expression (5), the refractive power when the sixth lens L6 is excluded, or in other words, the refractive power of the lenses from the first lens L1 up to the fifth lens L5, becomes relative small. Consequently, it becomes difficult to make the total length of the optical system small. Moreover, since it is not possible to correct the curvature of field favorably, it becomes difficult to achieve a high-definition image quality.

In a case of falling below a lower limit value of conditional expression (5), since the refractive power of the sixth lens L6 becomes relatively small, the shift in focus and the shift in the angle of deviation are susceptible to occur. Therefore, it is not preferable to fall below the lower limit value of conditional expression (5).

It is more preferable that the following conditional expression (5') be satisfied instead of conditional expression (5).

$$1.55<f15/f<4.0 \quad (5')$$

It is even more preferable that the following conditional expression (5") be satisfied instead of conditional expression (5) or (5').

$$1.6<f15/f<3.0 \quad (5")$$

Moreover, according to a preferable aspect of the present embodiment, it is preferable that the following conditional expression (6) be satisfied:

$$2.3<f45/f6<7.2 \quad (6)$$

where, f45 denotes a combined focal length of lenses from the fourth lens L4 up to the fifth lens L5, and f6 denotes a focal length of the sixth lens L6.

Conditional expression (6) is related to an appropriate ratio of f45 and f6. Moreover, conditional expression (6) is a conditional expression related to the arrangement of refractive power of the cemented lens CL1 and the sixth lens L6. By satisfying conditional expression (6), it is possible to correct the chromatic aberration favorably while suppressing the degradation of the image quality due to the manufacturing variation at the process of assembling the objective optical system.

In a case of exceeding an upper limit value of conditional expression (6), the refractive power of the cemented lens CL1 becomes small, and it is not possible to correct the chromatic aberration favorably. Therefore, it is not preferable to exceed the upper limit value of conditional expression (6). Moreover, since the refractive power of the sixth lens L6 become large, the curvature of field occurs. Consequently, it becomes difficult to achieve a high-definition image quality.

In a case of falling below a lower limit value of conditional expression (6), since the refractive power of the cemented lens CL1 becomes large, degradation of an optical performance due to decentering is susceptible to occur. Moreover, since the refractive power of the sixth lens L6 becomes small, the shift in focus and the shift in the angle of deviation are susceptible to occur. Therefore, it is not preferable to fall below the lower limit value of conditional expression (6).

It is more preferable that the following conditional expression (6') be satisfied instead of conditional expression (6).

$$2.4 < f45/f6 < 5.0 \quad (6')$$

It is even more preferable that the following conditional expression (6") be satisfied instead of conditional expression (6) or (6').

$$2.5 < f45/f6 < 4.0 \quad (6'')$$

Moreover, according to a preferable aspect of the present embodiment, it is preferable that the following conditional expression (7) be satisfied:

$$-500 < f2/f1 < -11 \quad (7)$$

where,
f2 denotes a focal length of the second lens L2, and
f1 denotes the focal length of the first lens L1.

Conditional expression (7) is related to an appropriate ratio of f2 and f1. Moreover, conditional expression (7) is a conditional expression related to the arrangement of refractive power of lenses in the front group FL. By satisfying conditional expression (7), it is possible to suppress the shift in the angle of view at the process of assembling the objective optical system, and to make small a front-end lens while correcting favorably the chromatic aberration and the coma aberration which occur in the first lens L1.

In a case of exceeding an upper limit value of conditional expression (7), since the refractive power of the second lens L2 becomes large, degradation of the optical performance due to decentering is susceptible to occur. Moreover, since the refractive power of the first lens L1 becomes small, it becomes difficult to make the first lens L1 small.

In a case of falling below a lower limit value of conditional expression (7), since the refractive power of the second lens L2 becomes small, correction of the chromatic aberration and the coma aberration which occur in the first lens L1 becomes difficult. Moreover, since the refractive power of the first lens L1 becomes large, the shift in the angle of view at the process of assembling the objective optical system is susceptible to occur. Falling below the lower limit value of conditional expression (7) leads to degradation of the optical performance.

It is more preferable that the following conditional expression (7') be satisfied instead of conditional expression (7).

$$-100 < f2/f1 < -12 \quad (7')$$

It is even more preferable that the following conditional expression (7") be satisfied instead of conditional expression (7) or (7').

$$-30 < f2/f1 < -12.5 \quad (7'')$$

Moreover, according to a preferable aspect of the present embodiment, it is preferable that the following conditional expression (8) be satisfied:

$$4.0 < f2/f3 < 200 \quad (8)$$

where,
f2 denotes the focal length of the second lens L2, and
f3 denotes the focal length of the third lens L3.

Conditional expression (8) is related to an appropriate ratio of f2 and f3. Moreover, conditional expression (8) is a conditional expression related to the arrangement of refractive power of the second lens L2 and the third lens L3. By satisfying conditional expression (8), since it is possible to correct the curvature of field favorably, it is possible to achieve a high-definition image quality.

In a case of exceeding an upper limit value of conditional expression (8), since the refractive power of the second lens L2 becomes small, the curvature of field occurs. Exceeding the upper limit value of conditional expression (8) leads to degradation of image quality. Moreover, since the refractive power of the third lens L3 becomes large, degradation of the optical performance due to decentering is susceptible to occur. Therefore, it is not preferable to exceed the upper limit value of conditional expression (8).

In a case of falling below a lower limit value of conditional expression (8), since the refractive power of the second lens L2 becomes large, degradation of the optical performance due to decentering is susceptible to occur. Moreover, the refractive power of the third lens L3 becomes small. In this case, since it is not possible to correct the curvature of field favorably, it becomes difficult to achieve a high-definition image quality.

It is more preferable that the following conditional expression (8') be satisfied instead of conditional expression (8).

$$4.1 < f2/f3 < 100 \quad (8')$$

It is even more preferable that the following conditional expression (8") be satisfied instead of conditional expression (8) or (8').

$$4.2 < f2/f3 < 30 \quad (8'')$$

Moreover, according to a preferable aspect of the present embodiment, it is preferable that the following conditional expression (9) be satisfied:

$$1.6 < f15/IH < 5.0 \quad (9)$$

where,
f15 denotes the combined focal length of lenses from the first lens L1 up to the fifth lens L5, and
IH denotes the maximum image height.

Conditional expression (9) is related to an appropriate ratio of f15 and IH. By satisfying conditional expression (9), it is possible to make the total length of the optical system small while suppressing the manufacturing variation at the process of assembling the objective optical system.

In a case of exceeding an upper limit value of conditional expression (9), since the focal length of lenses from the first lens L1 up to the fifth lens L5 becomes relatively large, it becomes difficult to make the total length of the optical system small. Moreover, the maximum image height becomes small. In this case, since the optical system becomes weak with respect to the manufacturing variation, degradation of the optical performance at the process of assembling the objective optical system is susceptible to occur.

In a case of falling below a lower limit value of conditional expression (9), the refractive power of lens groups excluding the sixth lens L6 becomes large. In this case, since the refractive power of the sixth lens L6 becomes relatively small, it becomes difficult to suppress the shift in focus and the shift in the angle of deviation. Moreover, since the maximum image height becomes high, it becomes difficult to make the optical system small-sized.

It is more preferable that the following conditional expression (9') be satisfied instead of conditional expression (9).

$$1.61 < f15/IH < 4.0 \tag{9'}$$

It is even more preferable that the following conditional expression (9") be satisfied instead of conditional expression (9) or (9').

$$1.62 < f15/IH < 3.0 \tag{9"}$$

Moreover, according to a preferable aspect of the present embodiment, it is preferable that the following conditional expression (10) is satisfied:

$$v4 - v5 > 20 \tag{10}$$

where,
v4 denotes Abbe's number for the fourth lens L4, and
v5 denotes Abbe's number for the fifth lens L5.

Conditional expression (10) is related to an appropriate range of a difference between v4 and v5. By satisfying conditional expression (10), since it is possible to correct the chromatic aberration favorably, it is possible to achieve a high-definition image quality.

It is more preferable that the following conditional expression (10') be satisfied instead of conditional expression (10).

$$v4 - v5 > 25 \tag{10'}$$

It is even more preferable that the following conditional expression (10") be satisfied instead of conditional expression (10).

$$v4 - v5 > 30 \tag{10"}$$

Examples of the present invention will be described below.

Example 1

Figure 2A:
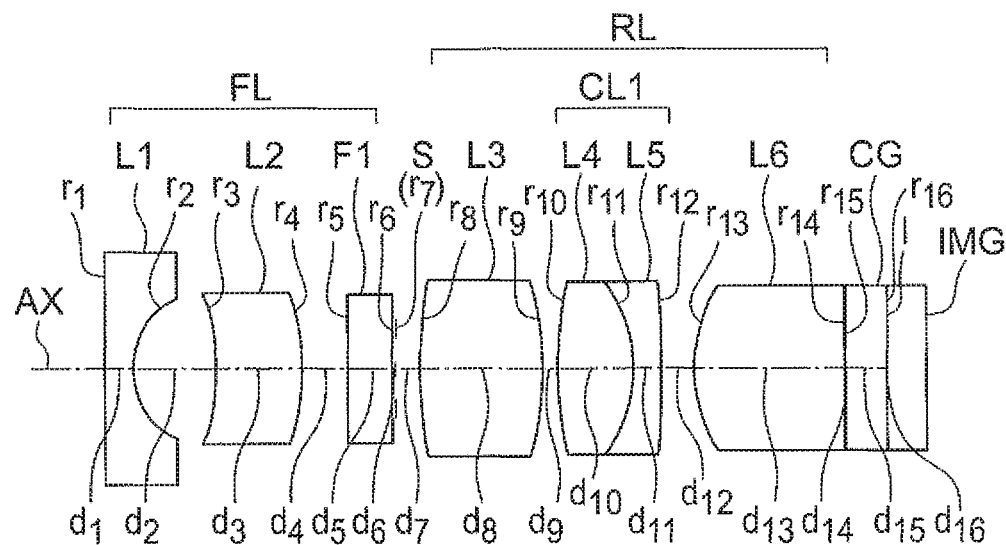
FIG. 2A is a diagram showing a cross-sectional view of a lens arrangement of an objective optical system for endoscope according to an example 1 of the present invention.
Figures 2B, 2C, 2D, 2E:
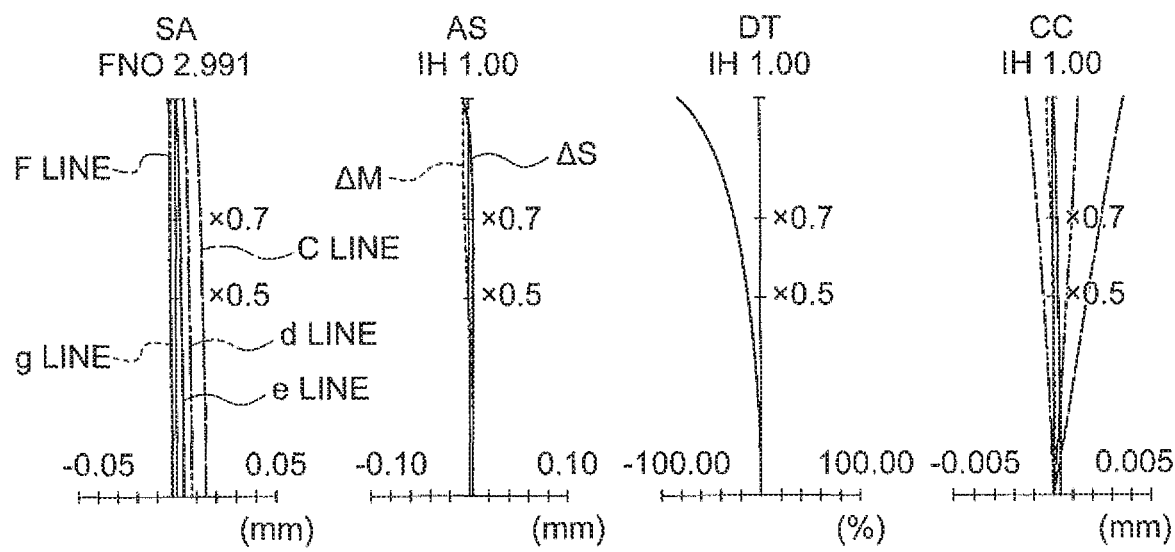
FIG. 2B, FIG. 2C, FIG. 2D, and FIG. 2E are aberration diagrams of the example 1.

An objective optical system for endoscope according to an example 1 will be described below. FIG. 2A is a diagram showing a cross-sectional view of a lens arrangement of the objective optical system for endoscope according to the present example.

The objective optical system for endoscope of the present example includes in order from an object side, a front group FL having negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a biconvex shape, a cemented lens CL1 of a fourth lens L4 having a positive refractive power and a biconvex shape and a fifth lens L5 having a negative refractive power and a meniscus shape with a convex surface directed toward the image side, and a sixth lens L6 having a positive refractive power and a planoconvex shape of which an image-plane side is a flat surface, which is cemented to a cover glass CG of an image pickup element IMG.

An absolute value of a radius of curvature of an image side of the second lens L2 is equal to an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG (yttrium aluminum garnet) laser cut coating is applied to an object side of the infra-red cut filter F1, and an LD laser cut coating is applied to an image side of the infra-red cut filter F1.

FIG. 2B, FIG. 2C, FIG. 2D, and FIG. 2E are aberration diagrams showing a spherical aberration (SA), an astigmatism (AS), a distortion (DT), and a chromatic aberration of magnification (CC) respectively, of the example 1.

The aberration diagrams are shown for the wavelengths of 546.07 nm (e-line), 435.83 nm (g-line), 486.13 nm (F-line), 656.27 nm (C-line), and 587.56 nm (d-line). Moreover, in each aberration diagram, IH denotes the maximum image height. Similar is a case for the aberration diagrams described below.

In the aberration diagrams, a horizontal axis indicates an aberration amount. The unit of aberration amount is mm for the spherical aberration, the astigmatism, and the chromatic aberration of magnification. Moreover, the unit of aberration amount is % for the distortion. Furthermore, the unit of IH is mm, and FNO denotes an F-number.

Example 2

Figure 3A:
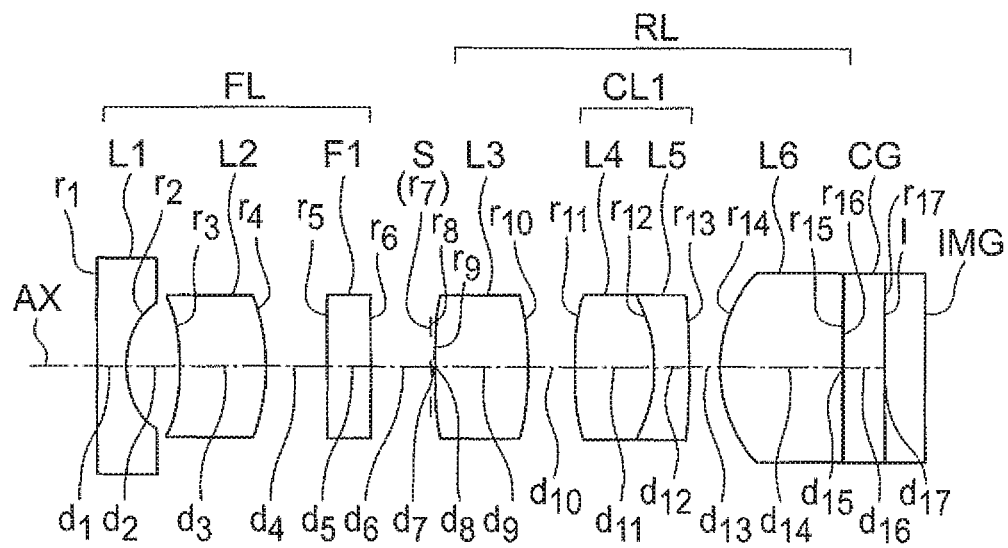
FIG. 3A is a diagram showing a cross-sectional view of a lens arrangement of an objective optical system for endoscope according to an example 2 of the present invention.
Figures 3B, 3C, 3D, 3E:
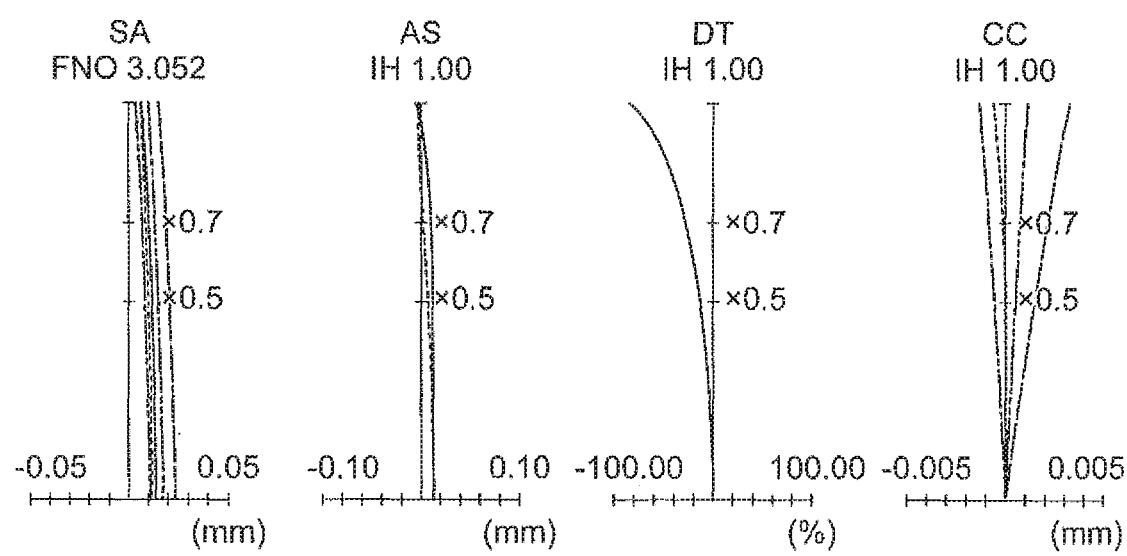
FIG. 3B, FIG. 3C, FIG. 3D, and FIG. 3E are aberration diagrams of the example 2.

An objective optical system for endoscope according to an example 2 will be described below. FIG. 3A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a biconvex shape, a cemented lens CL1 of a fourth lens L4 having a positive refractive power and a biconvex shape and a fifth lens L5 having a negative refractive power and a meniscus shape with a convex surface directed toward the image side, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens is larger than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 3B, FIG. 3C, FIG. 3D, and FIG. 3E are aberration diagrams showing a spherical aberration (SA), an astigmatism (AS), a distortion (DT), and a chromatic aberration of magnification (CC) respectively, of the example 2.

Example 3

Figure 4A:
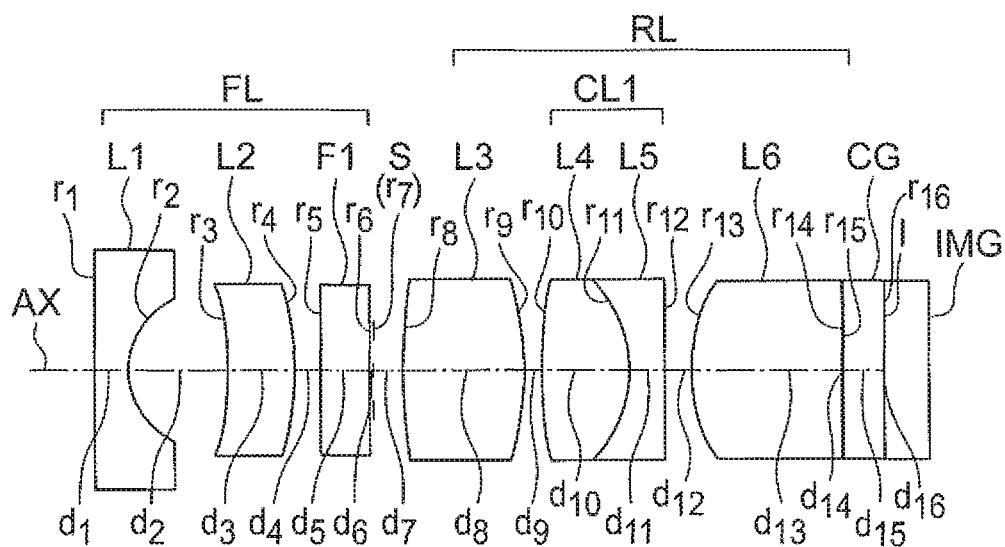
FIG. 4A is a diagram showing a cross-sectional view of a lens arrangement of an objective optical system for endoscope according to an example 3 of the present invention.
Figures 4B, 4C, 4D, 4E:
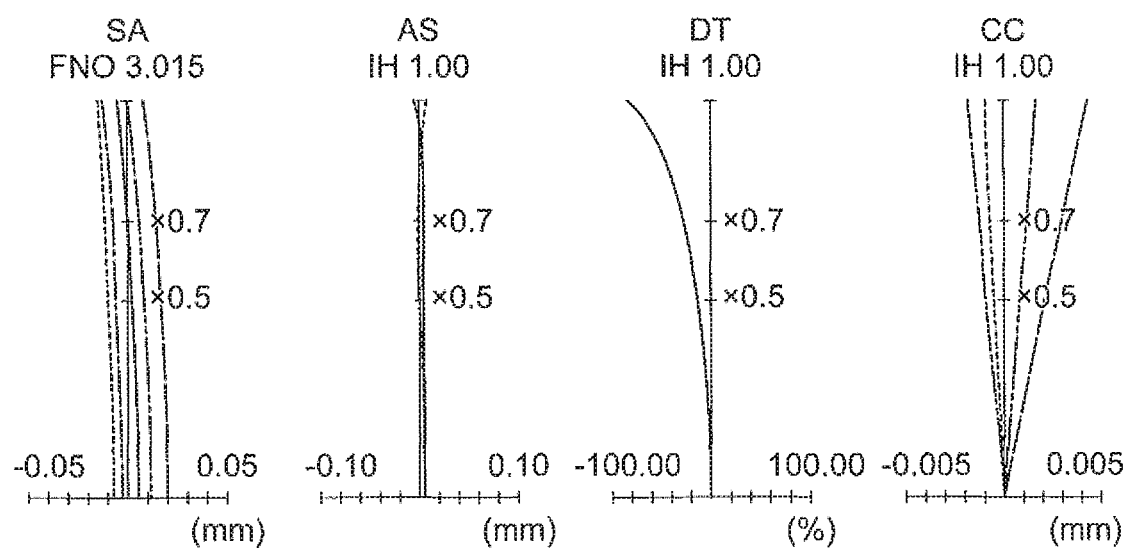
FIG. 4B, FIG. 4C, FIG. 4D, and FIG. 4E are aberration diagrams of the example 3.

An objective optical system for endoscope according to an example 3 will be described below. FIG. 4A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a biconvex shape, a cemented lens CL1 of a fourth lens L4 having a positive refractive power and a biconvex shape and a fifth lens L5 having a negative refractive power and a planoconcave shape of which an image side is a flat surface, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is smaller than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1. FIG. 4B, FIG. 4C, FIG. 4D, and FIG. 4E are aberration diagrams showing a spherical aberration (SA), an astigmatism (AS), a distortion (DT), and a chromatic aberration of magnification (CC) respectively, of the example 3.

Example 4

Figure 5A:
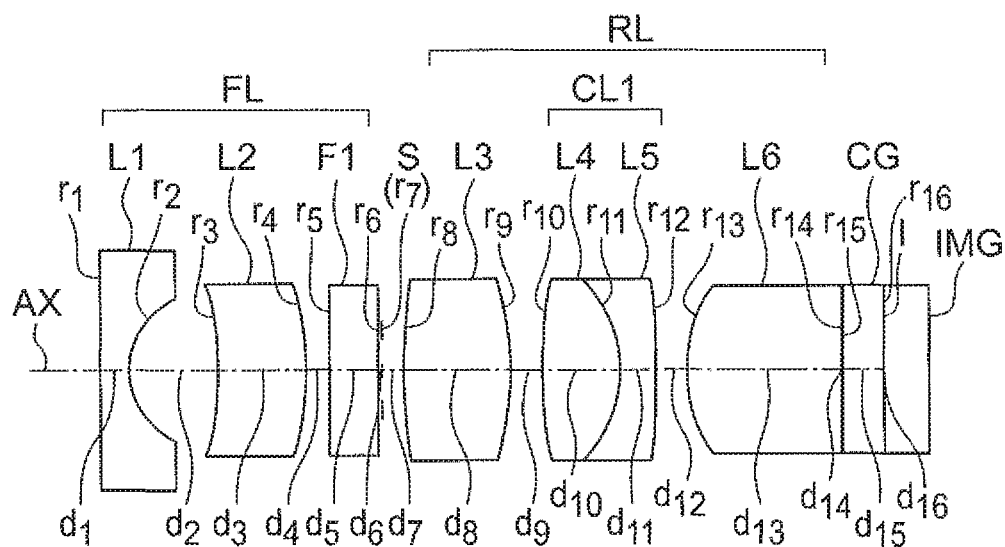
FIG. 5A is a diagram showing a cross-sectional view of a lens arrangement of an objective optical system for endoscope according to an example 4 of the present invention.
Figures 5B, 5C, 5D, 5E:
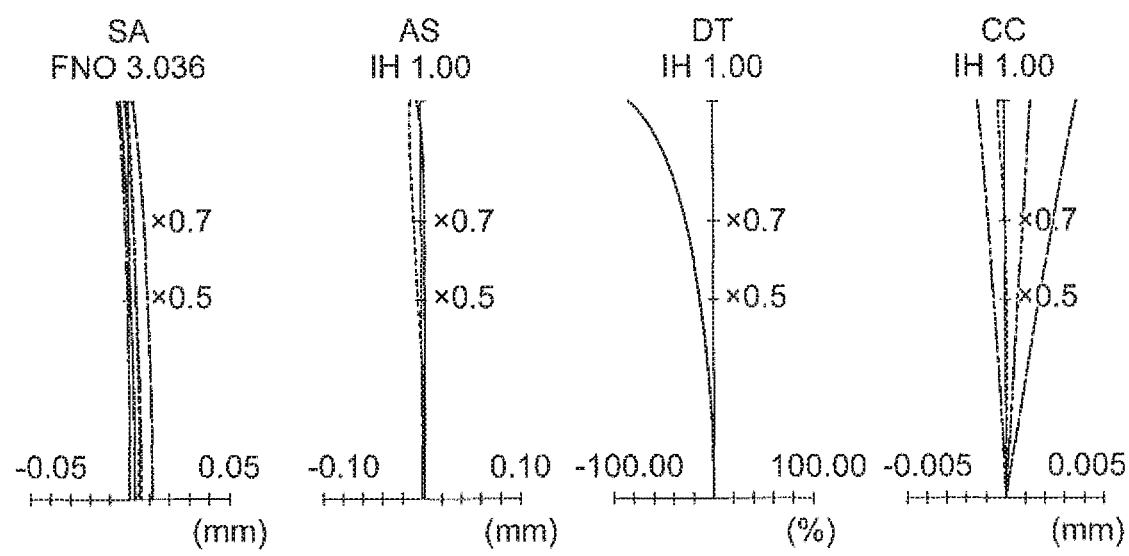
FIG. 5B, FIG. 5C, FIG. 5D, and FIG. 5E are aberration diagrams of the example 4.

An objective optical system for endoscope according to an example 4 will be described below. FIG. 5A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a biconvex shape, a cemented lens CL1 of a fourth lens L4 having a positive refractive power and a biconvex shape and a fifth lens L5 having a negative refractive power and a planoconcave shape of which an image side is a flat surface, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is larger than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 5B, FIG. 5C, FIG. 5D, and FIG. 5E are aberration diagrams showing a spherical aberration (SA), an astigmatism (AS), a distortion (DT), and a chromatic aberration of magnification (CC) respectively, of the example 4.

Example 5

Figure 6A:
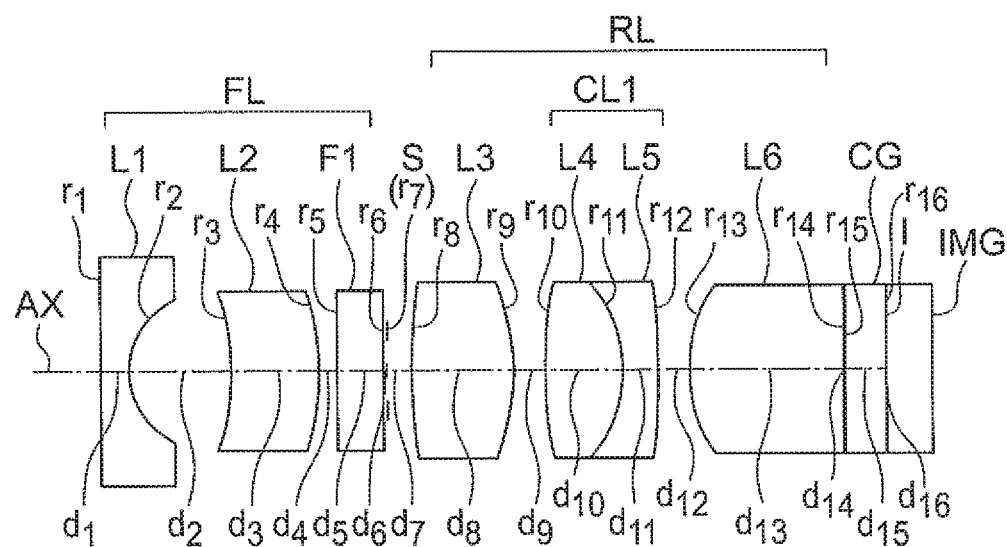
FIG. 6A is a diagram showing a cross-sectional view of a lens arrangement of an objective optical system for endoscope according to an example 5 of the present invention.
Figures 6B, 6C, 6D, 6E:
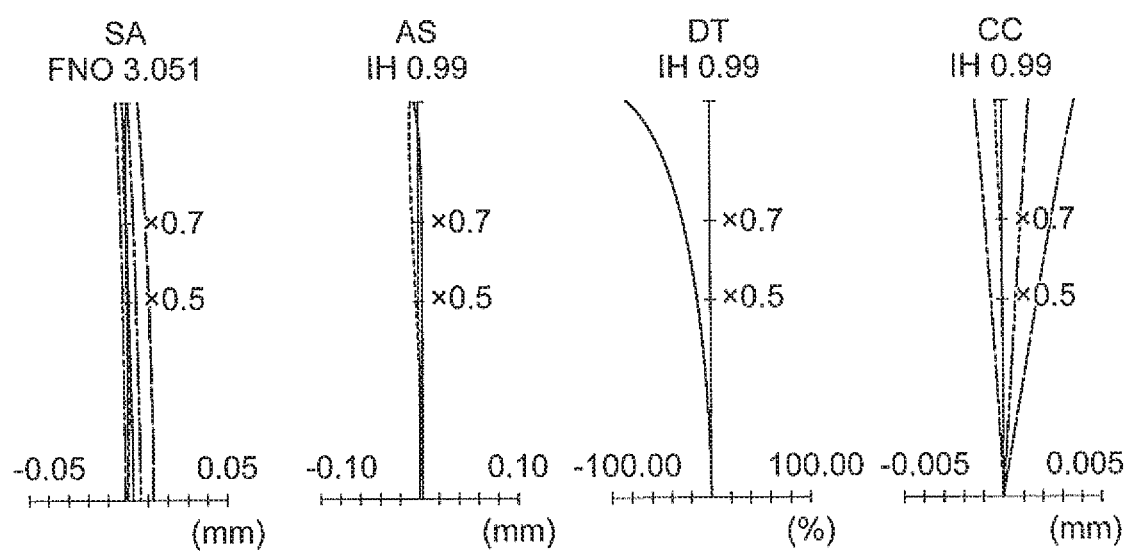
FIG. 6B, FIG. 6C, FIG. 6D, and FIG. 6E are aberration diagrams of the example 5.

An objective optical system for endoscope according to an example 5 will be described below. FIG. 6A is a diagram showing a cross-sectional view of a lens arrangement of the objective optical system for endoscope according to the present example.

The objective optical system for endoscope according to the preset example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a biconvex shape, a cemented lens CL1 of a fourth lens L4 having a positive refractive power and a biconvex shape and a fifth lens L5 having a negative refractive power and a planoconcave shape of which an image side is a flat surface, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is larger than an absoluter value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL include the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 6B, FIG. 6C, FIG. 6D, and FIG. 6E are aberration diagrams showing a spherical aberration (SA), an astigmatism (AS), a distortion (DT), and a chromatic aberration of magnification (CC) respectively, of the example 5.

Example 6

Figure 7A:
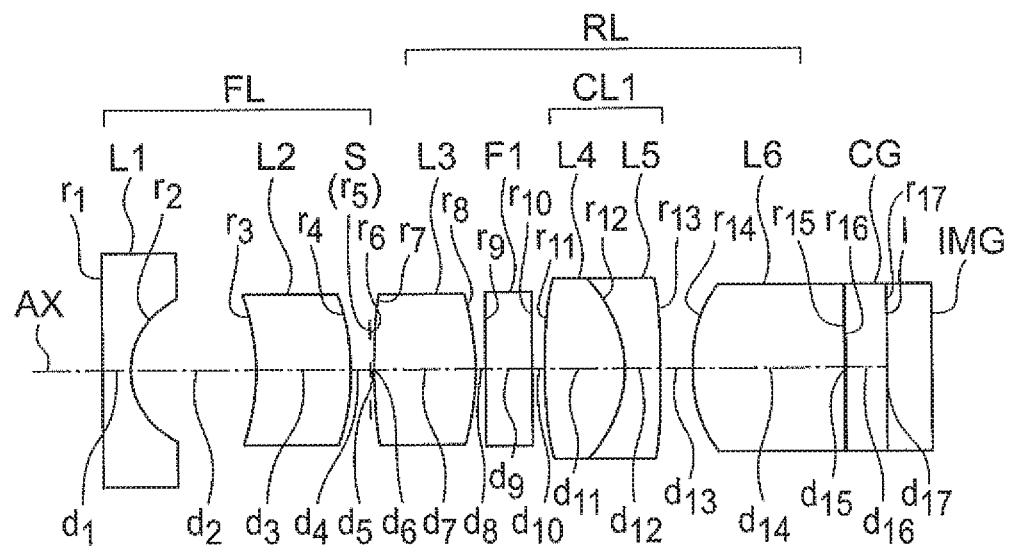
FIG. 7A is a diagram showing a cross-sectional view of a lens arrangement of an objective optical system for endoscope according to an example 6 of the present invention.
Figures 7B, 7C, 7D, 7E:
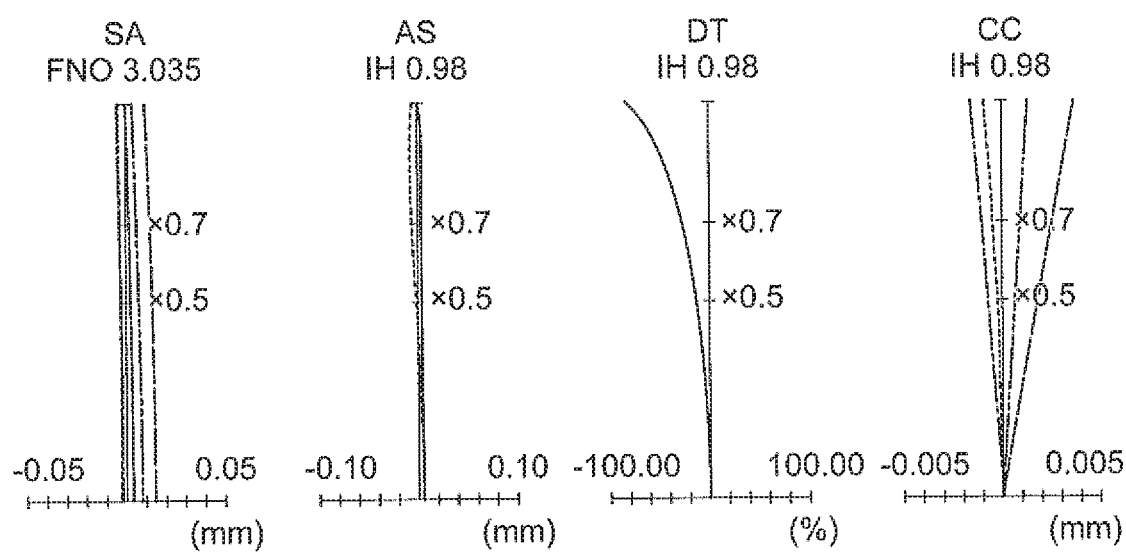
FIG. 7B, FIG. 7C, FIG. 7D, and FIG. 7E are aberration diagrams of the example 6.

An objective optical system for endoscope according to an example 6 will be described below. FIG. 7A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, the aperture stop S, a third lens L3 having a positive refractive power and a biconvex shape, an infra-red cut filter F1 which is a plane parallel plate, a cemented lens CL1 of a fourth lens L4 having a positive refractive power and a biconvex shape and a fifth lens L5 having a negative refractive power and a planoconcave shape of which an image side is a flat surface, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is larger than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power and the second lens L2 having a positive refractive power. The rear group RL includes the third lens L3 having a positive refractive power, the infra-red cut filter F1, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 7B, FIG. 7C, FIG. 7D, and FIG. 7E are aberration diagrams showing a spherical aberration (SA), an astigmatism (AS), a distortion (DT), and a chromatic aberration of magnification (CC) respectively, of the example 6.

Example 7

Figure 8A:
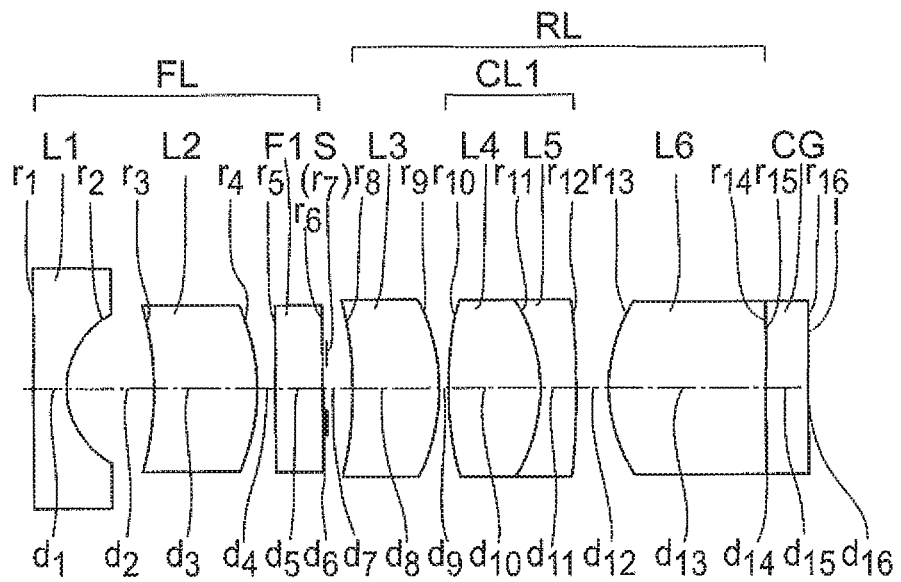
FIG. 8A is a diagram showing a cross-sectional view of a lens arrangement of an objective optical system for endoscope according to an example 7 of the present invention.
Figures 8B, 8C, 8D, 8E:
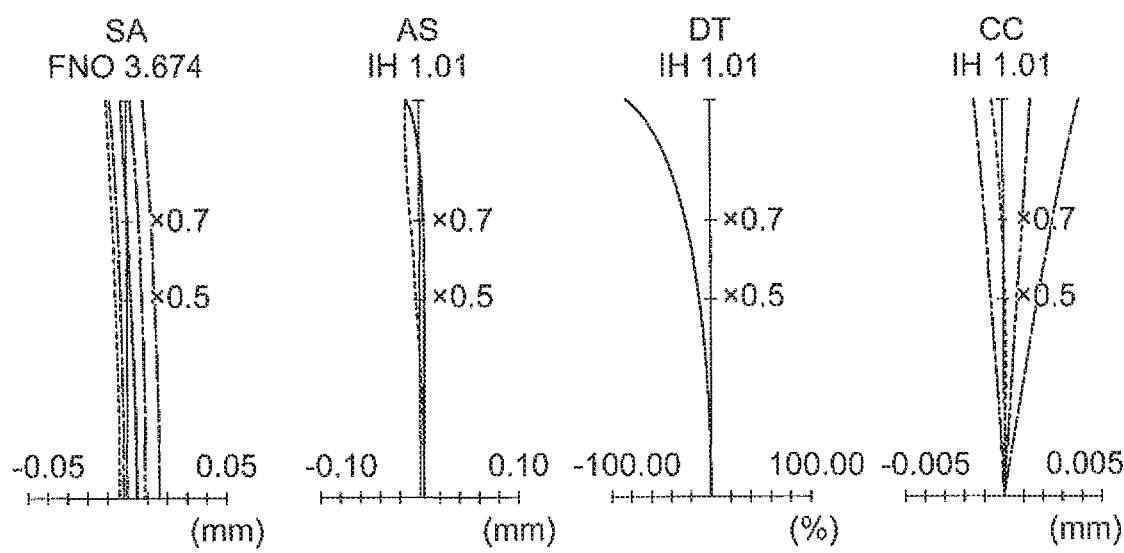
FIG. 8B, FIG. 8C, FIG. 8D, and FIG. 8E are aberration diagrams of the example 7.

An objective optical system for endoscope according to an example 7 will be described below. FIG. 8A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a meniscus shape with a convex surface directed toward the image side, a cemented lens CL1 of a fourth lens L4 having a positive refractive power and a biconvex shape and a fifth lens L5 having a negative refractive power and a meniscus shape with a convex surface directed toward the image side, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is smaller than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 8B, FIG. 8C, FIG. 8D, and FIG. 8E are aberration diagrams showing a spherical aberration (SA), an astigmatism (AS), a distortion (DT), and a chromatic aberration of magnification (CC) respectively, of the example 7.

Example 8

Figure 9A:
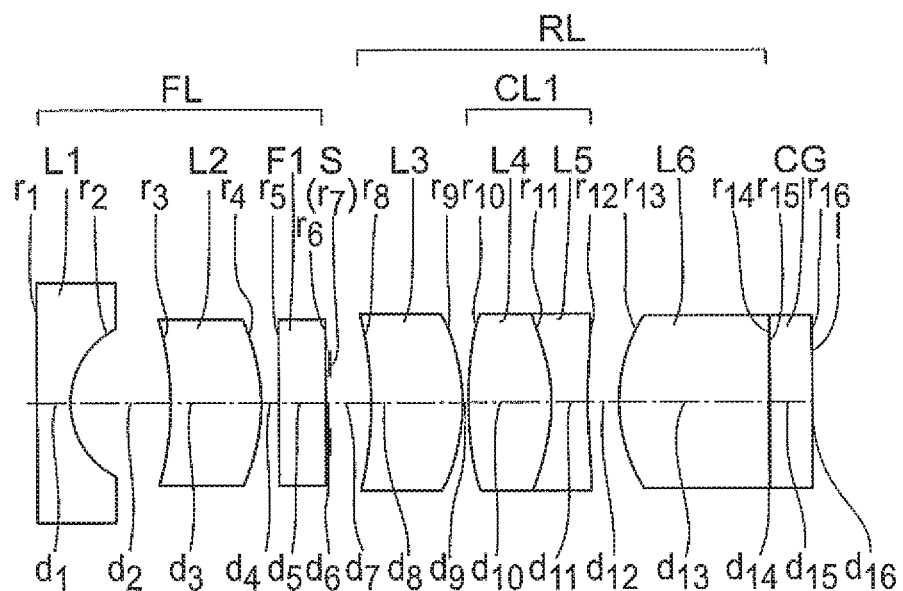
FIG. 9A is a diagram showing a cross-sectional view of a lens arrangement of an objective optical system for endoscope according to an example 8 of the present invention.
Figures 9B, 9C, 9D, 9E:
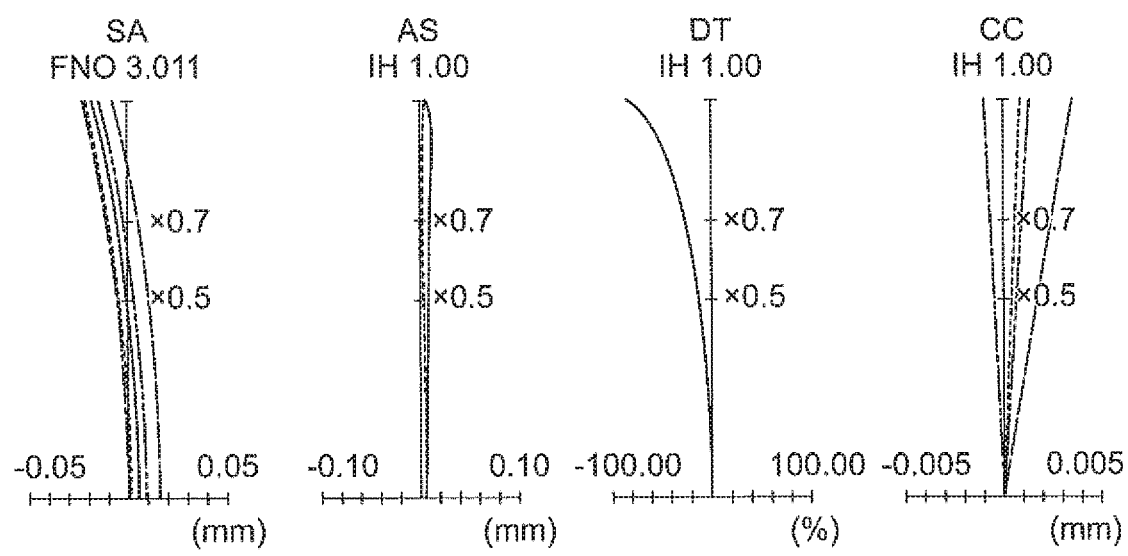
FIG. 9B, FIG. 9C, FIG. 9D, and FIG. 9E are aberration diagrams of the example 8.

An objective optical system for endoscope according to an example 8 will be described below. FIG. 9A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a meniscus shape with a convex surface directed toward the image side, a cemented lens CL1 of a fourth lens L4 having a positive refractive power and a biconvex shape and a fifth lens L5 having a negative refractive power and a biconcave shape, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is smaller than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 9B, FIG. 9C, FIG. 9D, and FIG. 9E are aberration diagrams showing a spherical aberration (SA), an astigmatism (AS), a distortion (DT), and a chromatic aberration of magnification (CC) respectively, of the example 8.

Example 9

Figure 10A:
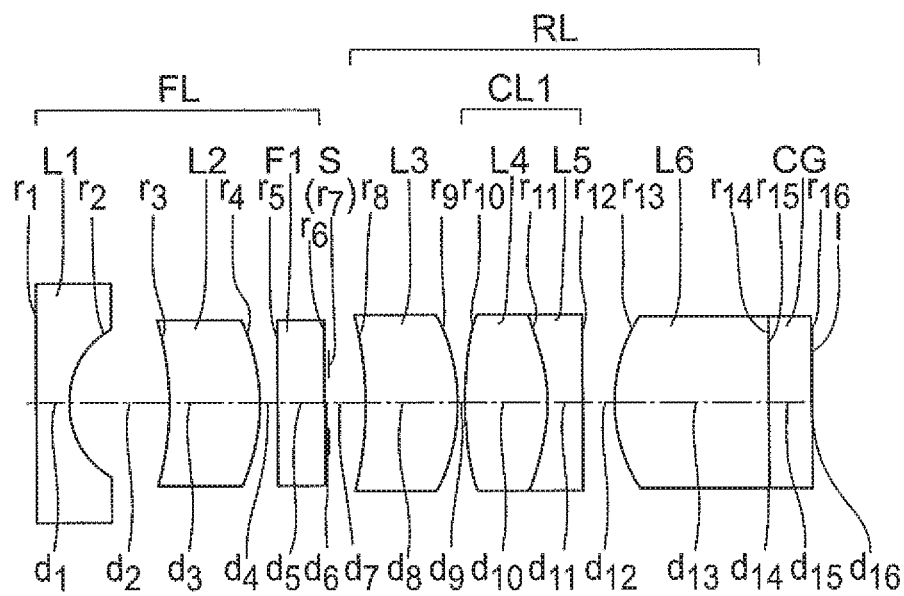
FIG. 10A is a diagram showing a cross-sectional view of a lens arrangement of an objective optical system for endoscope according to an example 9 of the present invention.
Figures 10B, 10C, 10D, 10E:
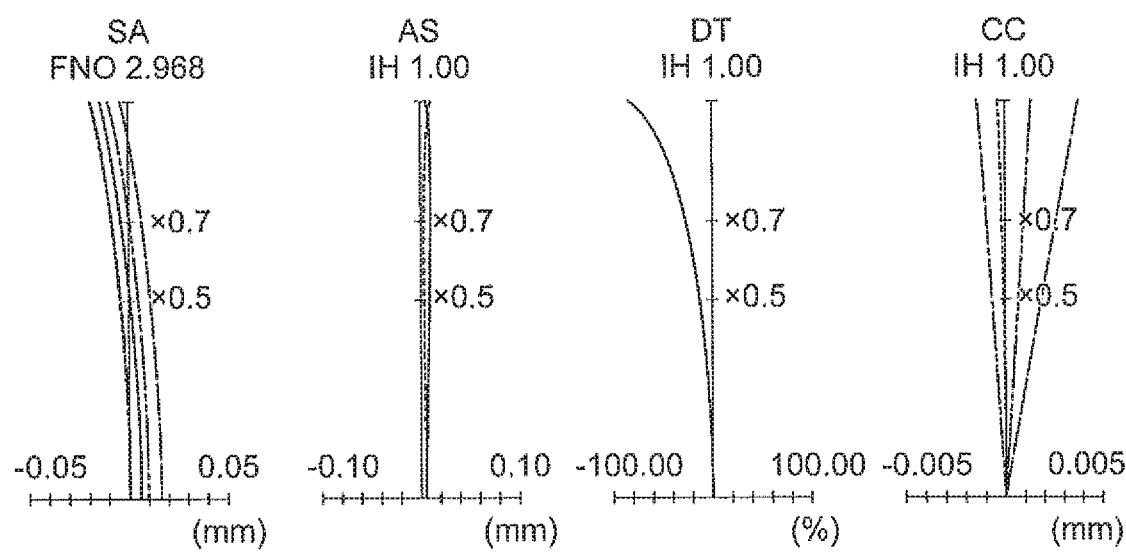
FIG. 10B, FIG. 10C, FIG. 10D, and FIG. 10E are aberration diagrams of the example 9.

An objective optical system for endoscope according to an example 9 will be described below. FIG. 10A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a meniscus shape with a convex surface directed toward the image side, a cemented lens CL1 of a fourth lens L4 having a positive refractive power and a biconvex shape and a fifth lens L5 having a negative refractive power and a planoconcave shape of which an image side is a flat surface, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is smaller than an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 10B, FIG. 10C, FIG. 10D, and FIG. 10E are aberration diagrams showing a spherical aberration (SA), an astigmatism (AS), a distortion (DT), and a chromatic aberration of magnification (CC) respectively, of the example 9.

Example 10

Figure 11A:
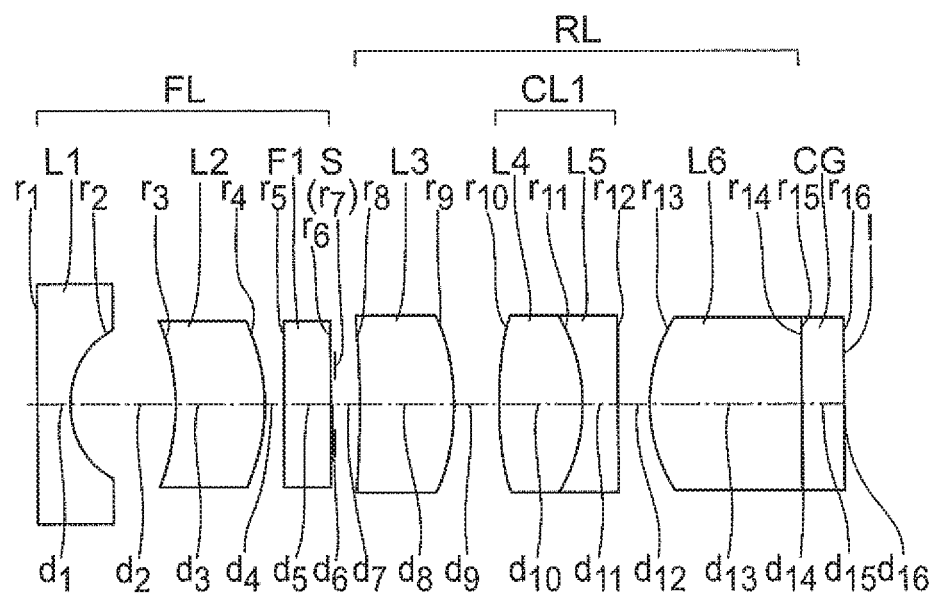
FIG. 11A is a diagram showing a cross-sectional view of a lens arrangement of an objective optical system for endoscope according to an example 10 of the present invention.
Figures 11B, 11C, 11D, 11E:
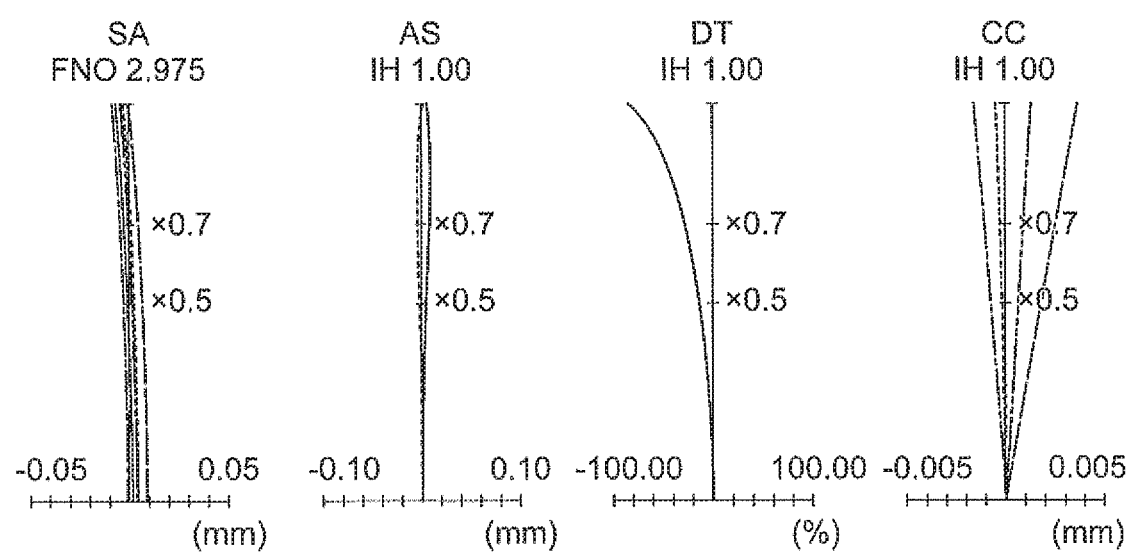
FIG. 11B, FIG. 11C, FIG. 11D, and FIG. 11E are aberration diagrams of the example 10.

An objective optical system for endoscope according to an example 10 will be described below. FIG. 11A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a meniscus shape with a convex surface directed toward the image side, a cemented lens CL1 of a fourth lens L4 having a positive refractive power and a biconvex shape and a fifth lens L5 having a negative refractive power and a meniscus shape with a convex surface directed toward the image side, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is equal to an absolute value of a radius of curvature of an object side of the second lens L2. An absolute value of a radius of curvature of an image side of the third lens L3 is smaller than an absolute value of a radius of curvature of an image side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 11B, FIG. 11C, FIG. 11D, and FIG. 11E are aberration diagrams showing a spherical aberration (SA), an astigmatism (AS), a distortion (DT), and a chromatic aberration of magnification (CC) respectively, of the example 10.

Example 11

Figure 12A:
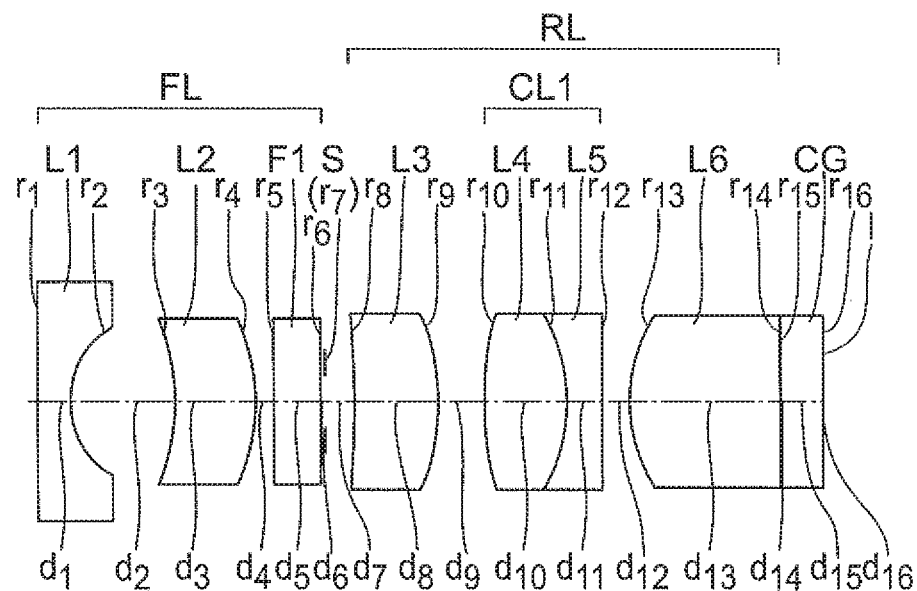
FIG. 12A is a diagram showing a cross-sectional view of a lens arrangement of an objective optical system for endoscope according to an example 11 of the present invention.
Figures 12B, 12C, 12D, 12E:
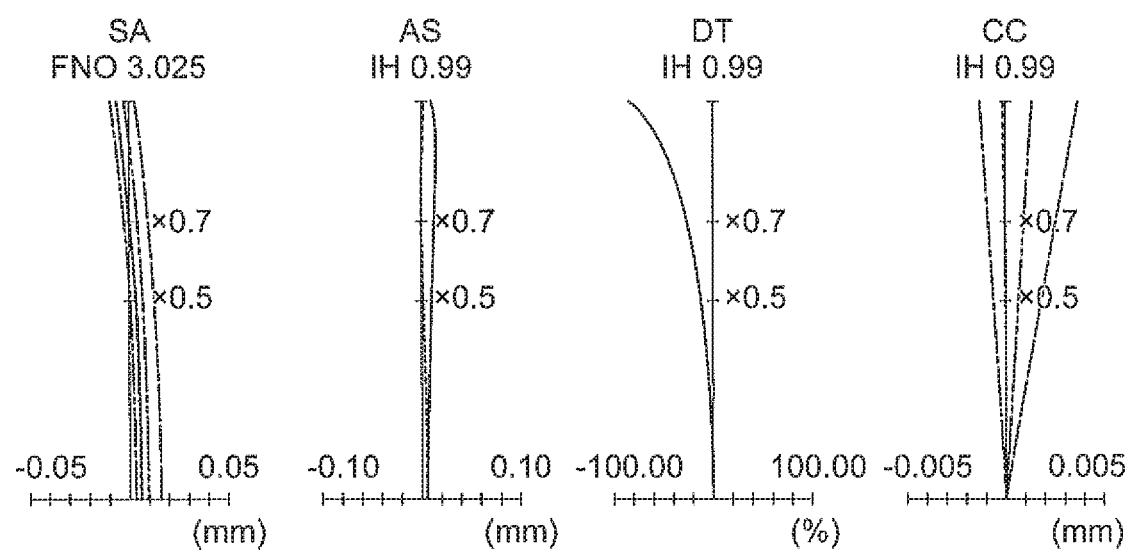
FIG. 12B, FIG. 12C, FIG. 12D, and FIG. 12E are aberration diagrams of the example 11.

An objective optical system for endoscope according to an example 11 will be described below. FIG. 12A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a meniscus shape with a convex surface directed toward the image side, a cemented lens CL1 of a fourth lens L4 having a positive refractive power and a biconvex shape and a fifth lens L5 having a negative refractive power and a planoconcave shape of which an image side is a flat surface, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is equal to an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 12B, FIG. 12C, FIG. 12D, and FIG. 12E are aberration diagrams showing a spherical aberration (SA), an astigmatism (AS), a distortion (DT), and a chromatic aberration of magnification (CC) respectively, of the example 11.

Example 12

Figure 13A:
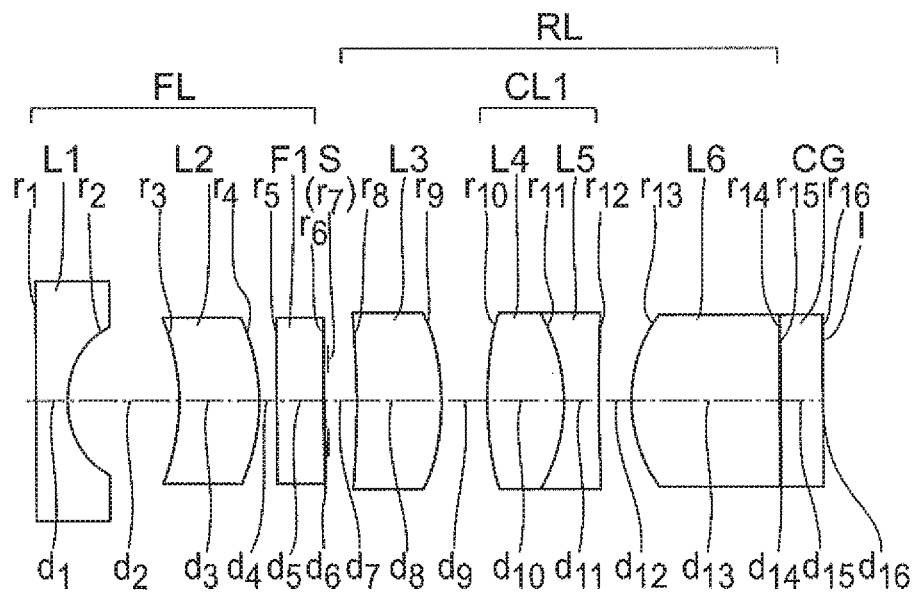
FIG. 13A is a diagram showing a cross-sectional view of a lens arrangement of an objective optical system for endoscope according to an example 12 of the present invention.
Figures 13B, 13C, 13D, 13E:
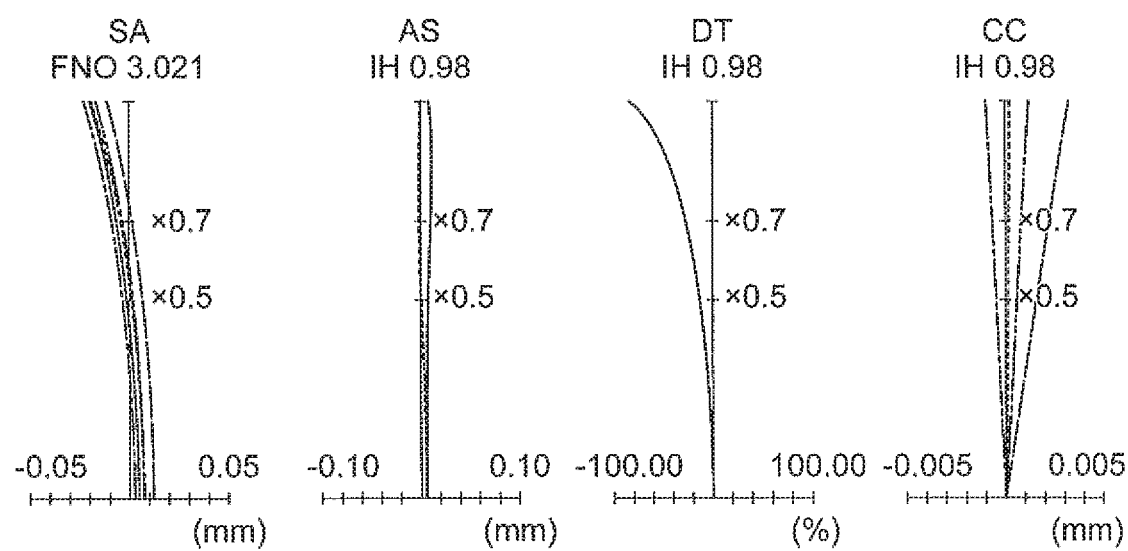
FIG. 13B, FIG. 13C, FIG. 13D, and FIG. 13E are aberration diagrams of the example 12.

An objective optical system for endoscope according to an example 12 will be described below. FIG. 13A is a diagram showing a cross-sectional view of a lens arrangement of the objective optical system for endoscope according to the present example.

The objective optical system for endoscope according to the present example includes in order from an object side, a front group FL having a negative refractive power, an aperture stop S, and a rear group RL having a positive refractive power.

The objective optical system for endoscope according to the present example includes in order from the object side, a first lens L1 having a negative refractive power and a planoconcave shape of which an object side is a flat surface, a second lens L2 having a positive refractive power and a meniscus shape with a convex surface directed toward an image side, an infra-red cut filter F1 which is a plane parallel plate, the aperture stop S, a third lens L3 having a positive refractive power and a meniscus shape with a convex surface directed toward the image side, a cemented lens CL1 of a fourth lens L4 having a positive refractive power and a biconvex shape and a fifth lens L5 having a negative refractive power and a biconcave shape, and a sixth lens L6 having a positive refractive power and a planoconvex shape with a flat surface directed toward an image-plane side, which is cemented to a cover glass CG of an image pickup element IMG.

An absolute value of a radius of curvature of an image side of the second lens L2 is equal to an absolute value of a radius of curvature of an object side of the second lens L2. An absolute value of a radius of curvature of an image side of the third lens L3 is smaller than an absolute value of a radius of curvature of an object side of the third lens L3.

The front group FL includes the first lens L1 having a negative refractive power, the second lens L2 having a positive refractive power, and the infra-red cut filter F1. The rear group RL includes the third lens L3 having a positive refractive power, the fourth lens L4 having a positive refractive power, the fifth lens L5 having a negative refractive power, and the sixth lens L6 having a positive refractive power.

A YAG laser cut coating is applied to an object side of the infra-red cut filter F1, and an LD laser cut coating is applied to an image side of the infra-red cut filter F1.

FIG. 13B, FIG. 13C, FIG. 13D, and FIG. 13E are aberration diagrams showing a spherical aberration (SA), an astigmatism (AS), a distortion (DT), and a chromatic aberration of magnification (CC) respectively, of the example 12.

Moreover, in the abovementioned examples, the description of the arrangement in which the sixth lens L6 and the cover glass CG of the image pickup element IMG are cemented was made. However, there is no problem even with an arrangement in which the sixth lens L6 and the cover glass CG of the image pickup element IMG are separated.

Moreover, in the abovementioned examples, the arrangement included the infra-red cut filter F1 which is a plane parallel plate. However, the arrangement may be without including the infra-red cut filter F1. Furthermore, the infra-red cut filter F1 is not required to be restricted to the plane parallel plate, and it may be a plane parallel plate not having a refractive power, such as a laser cut filter.

Numerical data of each example described above is shown below. In symbols, r denotes radius of curvature of each lens surface, d denotes a distance between respective lens surfaces, ne denotes a refractive index of each lens for a e-line, vd denotes an Abbe number for each lens, FNO denotes an F number, ω denotes a half angle of view, IH denotes an image height, and stop denotes an aperture stop.

Example 1

| Unit mm | | | | |
|---|---|---|---|---|
| Surface data | | | | |
| Surface no. | r | d | ne | vd |
| Object plane | ∞ | 23.2569 | | |
| 1 | ∞ | 0.5814 | 1.88815 | 40.76 |
| 2 | 1.5512 | 1.6280 | | |
| 3 | −4.3467 | 1.7675 | 1.93429 | 18.90 |
| 4 | −4.3467 | 0.9303 | | |
| 5 | ∞ | 0.9303 | 1.49557 | 75.00 |
| 6 | ∞ | 0.0698 | | |
| 7 (Stop) | ∞ | 0.4884 | | |
| 8 | 8.7120 | 2.4187 | 1.70442 | 30.13 |
| 9 | −5.6212 | 0.3023 | | |
| 10 | 8.3027 | 1.5350 | 1.73234 | 54.68 |
| 11 | −2.9350 | 0.5582 | 1.97189 | 17.47 |
| 12 | −22.1755 | 0.6326 | | |
| 13 | 3.1490 | 3.0234 | 1.51825 | 64.14 |
| 14 | ∞ | 0.0233 | 1.51500 | 64.00 |
| 15 | ∞ | 0.8140 | 1.50700 | 63.26 |
| 16 | ∞ | 0.0000 | | |
| Image pickup surface | ∞ | | | |
| Various data | | | | |
| f | | 1.000 | | |
| Fno | | 2.991 | | |
| ω | | 80.605 | | |
| IH | | 0.998 | | |

Example 2

| Unit mm | | | | |
|---|---|---|---|---|
| Surface data | | | | |
| Surface no. | r | d | ne | vd |
| Object plane | ∞ | 23.3425 | | |
| 1 | ∞ | 0.5836 | 1.88815 | 40.76 |
| 2 | 1.6990 | 1.1513 | | |
| 3 | −3.9900 | 1.8086 | 1.93429 | 18.90 |
| 4 | −4.6051 | 1.2726 | | |
| 5 | ∞ | 0.9337 | 1.49557 | 75.00 |
| 6 | ∞ | 1.2726 | | |
| 7 (Stop) | ∞ | 0.0700 | | |
| 8 | ∞ | 0.0000 | | |
| 9 | 9.1795 | 1.9518 | 1.80642 | 34.97 |
| 10 | −7.3019 | 0.9682 | | |
| 11 | 7.0590 | 1.6605 | 1.73234 | 54.68 |
| 12 | −3.1987 | 0.7417 | 1.97189 | 17.47 |
| 13 | −23.4257 | 0.6491 | | |
| 14 | 2.9461 | 2.5677 | 1.51825 | 64.14 |
| 15 | ∞ | 0.0233 | 1.51500 | 64.00 |
| 16 | ∞ | 0.8170 | 1.50700 | 63.26 |
| 17 | ∞ | 0.0000 | | |
| Image pickup surface | ∞ | | | |
| Various data | | | | |
| f | | 1.000 | | |
| Fno | | 3.052 | | |
| ω | | 80.276 | | |
| IH | | 1.001 | | |

Example 3

| Unit mm | | | | |
|---|---|---|---|---|
| Surface data | | | | |
| Surface no. | r | d | ne | vd |
| Object plane | ∞ | 22.0481 | | |
| 1 | ∞ | 0.5802 | 1.88815 | 40.76 |
| 2 | 1.5271 | 1.9077 | | |
| 3 | −5.7613 | 1.2765 | 1.93429 | 18.90 |
| 4 | −4.9162 | 0.4642 | | |
| 5 | ∞ | 0.9283 | 1.49557 | 75.00 |
| 6 | ∞ | 0.0696 | | |
| 7 (Stop) | ∞ | 0.5477 | | |
| 8 | 10.5798 | 2.3209 | 1.81264 | 25.42 |
| 9 | −5.6891 | 0.3017 | | |
| 10 | 9.0750 | 1.6695 | 1.88815 | 40.76 |
| 11 | −2.4174 | 0.6963 | 1.97189 | 17.47 |
| 12 | ∞ | 0.4766 | | |
| 13 | 3.1332 | 2.7850 | 1.51825 | 64.14 |
| 14 | ∞ | 0.0232 | 1.51500 | 64.00 |
| 15 | ∞ | 0.8123 | 1.50700 | 63.26 |
| 16 | ∞ | 0.0000 | | |
| Image pickup surface | ∞ | | | |
| Various data | | | | |
| f | | 1.000 | | |
| Fno | | 3.015 | | |
| ω | | 80.499 | | |
| IH | | 0.996 | | |

Example 4

Unit mm

Surface data

| Surface no. | r | d | ne | νd |
|---|---|---|---|---|
| Object plane | ∞ | 23.2124 | | |
| 1 | ∞ | 0.5803 | 1.88815 | 40.76 |
| 2 | 1.5483 | 1.7183 | | |
| 3 | −4.4180 | 1.7274 | 1.97189 | 17.47 |
| 4 | −5.2414 | 0.4642 | | |
| 5 | ∞ | 0.9285 | 1.49557 | 75.00 |
| 6 | ∞ | 0.0696 | | |
| 7 (Stop) | ∞ | 0.4178 | | |
| 8 | 9.5965 | 2.1113 | 1.76167 | 27.51 |
| 9 | −5.1377 | 0.6151 | | |
| 10 | 8.8656 | 1.5088 | 1.77621 | 49.60 |
| 11 | −2.4939 | 0.6964 | 1.97189 | 17.47 |
| 12 | −21.8440 | 0.6107 | | |
| 13 | 3.1430 | 3.0176 | 1.51825 | 64.14 |
| 14 | ∞ | 0.0232 | 1.51500 | 64.00 |
| 15 | ∞ | 0.8124 | 1.50700 | 63.26 |
| 16 | ∞ | 0.0000 | | |
| Image pickup surface | ∞ | | | |

Various data

| f | 1.000 |
|---|---|
| Fno | 3.036 |
| ω | 80.500 |
| IH | 0.996 |

Example 5

Unit mm

Surface data

| Surface no. | r | d | ne | νd |
|---|---|---|---|---|
| Object plane | ∞ | 23.0995 | | |
| 1 | ∞ | 0.5775 | 1.88815 | 40.76 |
| 2 | 1.5407 | 1.9851 | | |
| 3 | −4.6318 | 1.7556 | 1.97189 | 17.47 |
| 4 | −4.9130 | 0.3465 | | |
| 5 | ∞ | 0.9240 | 1.49557 | 75.00 |
| 6 | ∞ | 0.0693 | | |
| 7 (Stop) | ∞ | 0.4620 | | |
| 8 | 9.7958 | 1.9866 | 1.70442 | 30.13 |
| 9 | −5.2719 | 0.6484 | | |
| 10 | 7.8333 | 1.5246 | 1.75844 | 52.32 |
| 11 | −2.7875 | 0.6930 | 1.97189 | 17.47 |
| 12 | −26.3095 | 0.6087 | | |
| 13 | 3.1277 | 3.0029 | 1.51825 | 64.14 |
| 14 | ∞ | 0.0231 | 1.51500 | 64.00 |
| 15 | ∞ | 0.8085 | 1.50700 | 63.26 |
| 16 | ∞ | 0.0000 | | |
| Image pickup surface | ∞ | | | |

Various data

| f | 1.000 |
|---|---|
| Fno | 3.051 |
| ω | 80.497 |
| IH | 0.991 |

Example 6

Unit mm

Surface data

| Surface no. | r | d | ne | νd |
|---|---|---|---|---|
| Object plane | ∞ | 22.9341 | | |
| 1 | ∞ | 0.5734 | 1.88815 | 40.76 |
| 2 | 1.5297 | 2.4139 | | |
| 3 | −4.3408 | 1.8806 | 1.97189 | 17.47 |
| 4 | −5.0674 | 0.3440 | | |
| 5 (Stop) | ∞ | 0.0688 | | |
| 6 | ∞ | 0.0000 | | |
| 7 | 10.0719 | 2.0182 | 1.70442 | 30.13 |
| 8 | −5.3424 | 0.2225 | | |
| 9 | ∞ | 0.9174 | 1.49557 | 75.00 |
| 10 | ∞ | 0.2293 | | |
| 11 | 8.1047 | 1.5753 | 1.77621 | 49.60 |
| 12 | −2.5801 | 0.6880 | 1.97189 | 17.47 |
| 13 | −18.6603 | 0.6026 | | |
| 14 | 3.0319 | 2.9814 | 1.51825 | 64.14 |
| 15 | ∞ | 0.0229 | 1.51500 | 64.00 |
| 16 | ∞ | 0.8027 | 1.50700 | 63.26 |
| 17 | ∞ | 0.0000 | | |
| Image pickup surface | ∞ | | | |

Various data

| f | 1.000 |
|---|---|
| Fno | 3.035 |
| ω | 80.497 |
| IH | 0.984 |

Example 7

Unit mm

Surface data

| Surface no. | r | d | ne | νd |
|---|---|---|---|---|
| Object plane | ∞ | 16.4409 | | |
| 1 | ∞ | 0.5872 | 1.88815 | 40.76 |
| 2 | 1.5666 | 1.7380 | | |
| 3 | −6.0902 | 1.9964 | 1.97189 | 17.47 |
| 4 | −4.0867 | 0.3523 | | |
| 5 | ∞ | 0.9395 | 1.49557 | 75.00 |
| 6 | ∞ | 0.0705 | | |
| 7 (Stop) | ∞ | 0.5167 | | |
| 8 | −7.0978 | 1.6911 | 1.88815 | 40.76 |
| 9 | −3.9153 | 0.1879 | | |
| 10 | 7.3867 | 1.7850 | 1.75844 | 52.32 |
| 11 | −3.2436 | 0.7046 | 1.97189 | 17.47 |
| 12 | −17.1173 | 0.6341 | | |
| 13 | 3.1801 | 3.0533 | 1.51825 | 64.14 |
| 14 | ∞ | 0.0235 | 1.51500 | 64.00 |
| 15 | ∞ | 0.8220 | 1.50700 | 63.26 |
| 16 | ∞ | 0.0000 | | |
| Image pickup surface | ∞ | | | |

Various data

| f | 1.000 |
|---|---|
| Fno | 3.674 |
| ω | 80.974 |
| IH | 1.008 |

Example 8

| Unit mm | | | | |
|---|---|---|---|---|
| Surface data | | | | |
| Surface no. | r | d | ne | νd |
| Object plane | ∞ | 23.3213 | | |
| 1 | ∞ | 0.5830 | 1.88815 | 40.76 |
| 2 | 1.5932 | 1.9867 | | |
| 3 | −5.9937 | 1.7724 | 1.97189 | 17.47 |
| 4 | −4.1272 | 0.3498 | | |
| 5 | ∞ | 0.9329 | 1.49557 | 75.00 |
| 6 | ∞ | 0.0700 | | |
| 7 (Stop) | ∞ | 0.7976 | | |
| 8 | −8.0226 | 1.8191 | 1.88815 | 40.76 |
| 9 | −3.8074 | 0.0875 | | |
| 10 | 5.7073 | 1.6161 | 1.79196 | 47.37 |
| 11 | −4.0226 | 0.6996 | 1.97189 | 17.47 |
| 12 | 21.4755 | 0.6237 | | |
| 13 | 3.0931 | 2.9152 | 1.51825 | 64.14 |
| 14 | ∞ | 0.0233 | 1.51500 | 64.00 |
| 15 | ∞ | 0.8162 | 1.50700 | 63.26 |
| 16 | ∞ | 0.0000 | | |
| Image pickup surface | ∞ | | | |

| Various data | |
|---|---|
| f | 1.000 |
| Fno | 3.011 |
| ω | 80.500 |
| IH | 1.000 |

Example 9

| Unit mm | | | | |
|---|---|---|---|---|
| Surface data | | | | |
| Surface no. | r | d | ne | νd |
| Object plane | ∞ | 23.3989 | | |
| 1 | ∞ | 0.5850 | 1.88815 | 40.76 |
| 2 | 1.6086 | 1.9487 | | |
| 3 | −5.8220 | 1.7783 | 1.97189 | 17.47 |
| 4 | −4.0591 | 0.3510 | | |
| 5 | ∞ | 0.9360 | 1.49557 | 75.00 |
| 6 | ∞ | 0.0702 | | |
| 7 (Stop) | ∞ | 0.6880 | | |
| 8 | −8.0396 | 1.8251 | 1.88815 | 40.76 |
| 9 | −3.7979 | 0.1048 | | |
| 10 | 5.8883 | 1.5675 | 1.73234 | 54.68 |
| 11 | −3.8606 | 0.7020 | 1.97189 | 17.47 |
| 12 | ∞ | 0.6375 | | |
| 13 | 3.1724 | 2.9249 | 1.51825 | 64.14 |
| 14 | ∞ | 0.0234 | 1.51500 | 64.00 |
| 15 | ∞ | 0.8190 | 1.50700 | 63.26 |
| 16 | ∞ | 0.0000 | | |
| Image pickup surface | ∞ | | | |

| Various data | |
|---|---|
| f | 1.000 |
| Fno | 2.968 |
| ω | 80.500 |
| IH | 1.004 |

Example 10

| Unit mm | | | | |
|---|---|---|---|---|
| Surface data | | | | |
| Surface no. | r | d | ne | νd |
| Object plane | ∞ | 23.2251 | | |
| 1 | ∞ | 0.5806 | 1.88815 | 40.76 |
| 2 | 1.5793 | 2.0327 | | |
| 3 | −4.2228 | 1.7187 | 1.97189 | 17.47 |
| 4 | −4.2228 | 0.3484 | | |
| 5 | ∞ | 0.9290 | 1.49557 | 75.00 |
| 6 | ∞ | 0.0697 | | |
| 7 (Stop) | ∞ | 0.4767 | | |
| 8 | −46.9600 | 1.8116 | 1.88815 | 40.76 |
| 9 | −4.7495 | 0.9020 | | |
| 10 | 6.2735 | 1.5793 | 1.75844 | 52.32 |
| 11 | −3.3749 | 0.6968 | 1.97189 | 17.47 |
| 12 | −68.3554 | 0.5880 | | |
| 13 | 3.3625 | 2.9031 | 1.51825 | 64.14 |
| 14 | ∞ | 0.0232 | 1.51500 | 64.00 |
| 15 | ∞ | 0.8129 | 1.50700 | 63.26 |
| 16 | ∞ | 0.0000 | | |
| Image pickup surface | ∞ | | | |

| Various data | |
|---|---|
| f | 1.000 |
| Fno | 2.975 |
| ω | 80.501 |
| IH | 0.996 |

Example 11

| Unit mm | | | | |
|---|---|---|---|---|
| Surface data | | | | |
| Surface no. | r | d | ne | νd |
| Object plane | ∞ | 23.1735 | | |
| 1 | ∞ | 0.5793 | 1.88815 | 40.76 |
| 2 | 1.5758 | 2.0885 | | |
| 3 | −3.8188 | 1.5526 | 1.97189 | 17.47 |
| 4 | −3.8188 | 0.3476 | | |
| 5 | ∞ | 0.9269 | 1.49557 | 75.00 |
| 6 | ∞ | 0.0695 | | |
| 7 (Stop) | ∞ | 0.5611 | | |
| 8 | −25.3515 | 1.6685 | 1.88815 | 40.76 |
| 9 | −4.4402 | 0.9267 | | |
| 10 | 6.0430 | 1.5758 | 1.75844 | 52.32 |
| 11 | −3.4688 | 0.6952 | 1.97189 | 17.47 |
| 12 | ∞ | 0.5463 | | |
| 13 | 3.2877 | 2.8967 | 1.51825 | 64.14 |
| 14 | ∞ | 0.0232 | 1.51500 | 64.00 |
| 15 | ∞ | 0.8111 | 1.50700 | 63.26 |
| 16 | ∞ | 0.0000 | | |
| Image pickup surface | ∞ | | | |

| Various data | |
|---|---|
| f | 1.000 |
| Fno | 3.025 |
| ω | 80.501 |
| IH | 0.994 |

Example 12

| | | Unit mm | | |
|---|---|---|---|---|
| | | Surface data | | |
| Surface no. | r | d | ne | vd |
| Object plane | ∞ | 22.8830 | | |
| 1 | ∞ | 0.5721 | 1.88815 | 40.76 |
| 2 | 1.5560 | 2.2046 | | |
| 3 | −4.0014 | 1.5332 | 1.97189 | 17.47 |
| 4 | −4.0014 | 0.3432 | | |
| 5 | ∞ | 0.9153 | 1.49557 | 75.00 |
| 6 | ∞ | 0.0686 | | |
| 7 (Stop) | ∞ | 0.5661 | | |
| 8 | −30.4732 | 1.6476 | 1.88815 | 40.76 |
| 9 | −4.0895 | 0.8465 | | |
| 10 | 5.3300 | 1.4638 | 1.65425 | 58.55 |
| 11 | −3.6311 | 0.6865 | 1.97189 | 17.47 |
| 12 | 44.0440 | 0.6250 | | |
| 13 | 2.8520 | 2.8604 | 1.51825 | 64.14 |
| 14 | ∞ | 0.0229 | 1.51500 | 64.00 |
| 15 | ∞ | 0.8009 | 1.50700 | 63.26 |
| 16 | ∞ | 0.0000 | | |
| Image pickup surface | ∞ | | | |

| Various data | |
|---|---|
| f | 1.000 |
| Fno | 3.021 |
| ω | 80.502 |
| IH | 0.982 |

Next, values of conditional expressions in each example are given below.
(1) f3/d6
(2) |f1/f|
(3) f35/f12
(4) R6L/R1R
(5) f15/f
(6) f45/f6
(7) f2/f1
(8) f2/f3
(9) f15/IH
(10) vd4−vd5

Conditional Expression

| | Example1 | Example2 | Example3 |
|---|---|---|---|
| (1) | 1.72 | 2.07 | 1.75 |
| (2) | 1.75 | 1.91 | 1.72 |
| (3) | −1.58 | −1.65 | −1.52 |
| (4) | 2.03 | 1.73 | 2.05 |
| (5) | 1.70 | 1.64 | 1.64 |
| (6) | 3.09 | 2.41 | 2.50 |
| (7) | −13.56 | −39.77 | −12.06 |
| (8) | 4.54 | 14.29 | 4.26 |
| (9) | 1.71 | 1.64 | 1.64 |
| (10) | 37.21 | 37.21 | 23.29 |

| | Example4 | Example5 | Example6 |
|---|---|---|---|
| (1) | 1.55 | 1.71 | 1.76 |
| (2) | 1.74 | 1.73 | 1.72 |
| (3) | −1.84 | −1.71 | −1.86 |
| (4) | 2.03 | 2.03 | 1.98 |
| (5) | 1.70 | 1.70 | 1.73 |
| (6) | 2.95 | 2.75 | 2.32 |
| (7) | −488.48 | −23.11 | −65.61 |
| (8) | 181.83 | 7.79 | 21.57 |
| (9) | 1.71 | 1.72 | 1.76 |
| (10) | 32.13 | 34.85 | 32.13 |

| | Example7 | Example8 | Example9 |
|---|---|---|---|
| (1) | 2.58 | 2.33 | 2.30 |
| (2) | 1.76 | 1.79 | 1.81 |
| (3) | −0.87 | −0.93 | −0.89 |
| (4) | 2.03 | 1.94 | 1.97 |
| (5) | 1.70 | 1.69 | 1.67 |
| (6) | 1.74 | 2.72 | 2.36 |
| (7) | −4.86 | −5.18 | −5.09 |
| (8) | 1.09 | 1.37 | 1.37 |
| (9) | 1.68 | 1.69 | 1.66 |
| (10) | 34.85 | 29.90 | 37.21 |

| | Example10 | Example11 | Example12 |
|---|---|---|---|
| (1) | 2.01 | 2.02 | 1.81 |
| (2) | 1.78 | 1.77 | 1.75 |
| (3) | −1.43 | −1.40 | −1.52 |
| (4) | 2.13 | 2.09 | 1.83 |
| (5) | 1.60 | 1.62 | 1.77 |
| (6) | 2.01 | 2.22 | 7.14 |
| (7) | −12.18 | −11.05 | −12.44 |
| (8) | 3.71 | 3.36 | 4.22 |
| (9) | 1.60 | 1.63 | 1.80 |
| (10) | 34.85 | 34.85 | 41.08 |

The abovementioned objective optical system for endoscope may satisfy a plurality of arrangements simultaneously. Making such arrangement is preferable for achieving a favorable an objective optical system for endoscope. Moreover, combinations of preferable arrangements are arbitrary. For each conditional expression, only the upper limit value or the lower limit value of a numerical range of a conditional expression further restricted, may be limited.

The embodiment and various examples of the present invention are described above. However, the present invention is not restricted to these embodiment and examples, and embodiments formed by combining arrangement of these embodiment and examples without departing from the scope of the present invention are also included in the category of the present invention.

According to the present embodiment, an effect that it is possible to provide an objective optical system for endoscope which is small-sized and which enables to achieve a wide angle of view and high-definition image quality while suppressing the degradation of optical performance due to the shift in focus, the shift in the angle of view, and the shift in the angle of deviation caused due to a manufacturing error at the process of assembling the objective optical system.

As described heretofore, the present invention is useful for an objective optical system for endoscope which is small-sized and which enables to achieve a wide angle of view and high-definition image quality while reducing the shift in focus, the shift in the angle of view, and the shift in the angle of deviation at the process of assembling the objective optical system.

What is claimed is:

1. An objective optical system for an endoscope, the objective optical system consisting of, in order from an object side to an image side:

a front group having a negative refractive power;

an aperture stop; and a rear group having a positive refractive power, wherein:

the front group consists of a first lens which is a single lens having a negative refractive power and a second lens which is a single lens having a positive refractive power, the rear group consists of (i) a third lens which is a single lens having a positive refractive power, (ii) a cemented lens of a fourth lens having a positive refractive power and a fifth lens having a negative refractive power, the cemented lens being disposed on the image side with respect to the third lens, and (iii) a sixth lens having a positive refractive power, the sixth lens being disposed on the image side with respect to the cemented lens, an object-side surface of the first lens is a flat surface, a shape of the second lens is a meniscus shape having a convex surface directed toward the image side, the sixth lens is cemented to a plane parallel plate, and the following conditional expressions (1) and (2) are satisfied:

$$1.0 < f3/d6 < 2.8 \quad (1)$$

$$1.7 < |f1/f| < 10 \quad (2)$$

where, f3 denotes a focal length of the third lens, d6 denotes a thickness of the sixth lens, f1 denotes a focal length of the first lens, and f denotes an overall focal length of the objective optical system.

2. The objective optical system according to claim 1, wherein the following conditional expression (3) is satisfied:

$$-5.0 < f35/f12 < -1.3 \quad (3)$$

where, f35 denotes a combined focal length of lenses from the third lens up to the fifth lens, and f12 denotes a combined focal length of lenses from the first lens up to the second lens.

3. The objective optical system according to claim 1, wherein the following conditional expression (4) is satisfied:

$$0.5 < R6L/R1R < 2.4 \quad (4)$$

where,

R6L denotes a radius of curvature of an object-side surface of the sixth lens, and R1R denotes a radius of curvature of an image-side surface of the first lens.

4. The objective optical system according to claim 1, wherein the following conditional expression (5) is satisfied:

$$1.55 < f15/f < 5.0 \quad (5)$$

where, f15 denotes a combined focal length of lenses from the first lens up to the fifth lens.

5. The objective optical system according to claim 1, wherein the following conditional expression (6) is satisfied:

$$2.3 < f45/f6 < 7.2 \quad (6)$$

where, f45 denotes a combined focal length of lenses from the fourth lens up to the fifth lens, and f6 denotes a focal length of the sixth lens.

6. The objective optical system according to claim 1, wherein the following conditional expression (7) is satisfied:

$$-500 < f2/f1 < -11 \quad (7)$$

where, f2 denotes a focal length of the second lens.

7. The objective optical system according to claim 1, wherein the following conditional expression (8) is satisfied:

$$4.0 < f2/f3 < 200 \quad (8)$$

where, f2 denotes a focal length of the second lens.

8. The objective optical system according to claim 1, wherein the following conditional expression (9) is satisfied:

$$1.6 < f15/IH < 5.0 \quad (9)$$

where, f15 denotes a combined focal length of lenses from the first lens up to the fifth lens, and IH denotes the maximum image height.

9. The objective optical system according to claim 1, wherein the following conditional expression (10) is satisfied:

$$v4 - v5 > 20 \quad (10)$$

where, v4 denotes Abbe's number for the fourth lens, and v5 denotes Abbe's number for the fifth lens.

* * * * *